US011896254B2

(12) United States Patent
Boone et al.

(10) Patent No.: US 11,896,254 B2
(45) Date of Patent: *Feb. 13, 2024

(54) FORCEPS INCLUDING A PRE-LOADED HANDLE LATCH

(71) Applicant: GYRUS ACMI, INC., Southborough, MA (US)

(72) Inventors: Eric J. Boone, Saint Michael, MN (US); Christian J. Fiksen, Maple Grove, MN (US); Zane R. Ward, Minneapolis, MN (US); Hanam Pham, Minneapolis, MN (US); Jeffrey Nelson, Plymouth, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 704 days.

This patent is subject to a terminal disclaimer.

(21) Appl. No.: 17/089,264

(22) Filed: Nov. 4, 2020

(65) Prior Publication Data

US 2021/0045763 A1 Feb. 18, 2021

Related U.S. Application Data

(63) Continuation of application No. 15/941,205, filed on Mar. 30, 2018, now Pat. No. 10,849,641.

(51) Int. Cl.
*A61B 17/29* (2006.01)
*A61B 17/28* (2006.01)
(Continued)

(52) U.S. Cl.
CPC ...... *A61B 17/2833* (2013.01); *A61B 17/2909* (2013.01); *A61B 18/1445* (2013.01);
(Continued)

(58) Field of Classification Search
CPC ............ A61B 17/1606; A61B 17/0206; A61B 17/2283; A61B 17/3201; A61B 17/22;
(Continued)

(56) References Cited

U.S. PATENT DOCUMENTS

| 1,198,958 A | 9/1916 | Risley |
| 2,042,985 A | 6/1936 | Gardella |

(Continued)

FOREIGN PATENT DOCUMENTS

| CN | 101330849 A | 12/2008 |
| CN | 105188573 A | 12/2015 |

(Continued)

OTHER PUBLICATIONS

"European Application Serial No. 21156718.5, Extended European Search Report dated Jun. 10, 2021", 8 pgs.

(Continued)

*Primary Examiner* — Kathleen S Holwerda
(74) *Attorney, Agent, or Firm* — Schwegman Lundberg & Woessner, P.A.

(57) ABSTRACT

A surgical device comprising: a closure assembly including: (a) a latch unit comprising: (A) a hook latch, having a home position, (B) a forward bias constraint, (C) a rearward bias constraint, and (D) a bias member extending between the forward bias constraint and the rearward bias constraint so that the bias member has a pre-load when the hook latch is in the home position; (b) a movement unit including a bar that is movable relative to the latch unit so that the bar is movable in a prescribed motion into contact with the latch unit to create a locked state; and wherein the bar moves into contact with the hook latch driving the hook latch in a first direction, away relative to the home position, and then the hook latch is moved by the bar in a second direction relative to the home position, and a loading of the bias member is (Continued)

increased from the pre-load when the hook latch is moved in either the first direction away from the home position or the second direction away from the home position.

18 Claims, 12 Drawing Sheets

(51) Int. Cl.
  *A61B 18/14* (2006.01)
  *A61B 18/16* (2006.01)
  *A61B 18/00* (2006.01)
(52) U.S. Cl.
  CPC .......... *A61B 18/1447* (2013.01); *A61B 18/16* (2013.01); *A61B 2017/2925* (2013.01); *A61B 2017/2946* (2013.01); *A61B 2018/00589* (2013.01); *A61B 2018/00595* (2013.01); *A61B 2018/00601* (2013.01); *A61B 2018/00982* (2013.01); *A61B 2018/1452* (2013.01)
(58) Field of Classification Search
  CPC .... A61B 2017/1125; A61B 2017/2837; A61B 18/1442; A61B 18/1445; A61B 18/1447; A61B 10/06; A61B 2017/2946; A61B 2017/2925; A61B 2018/1455; A61B 2018/1462; A61B 17/29
  See application file for complete search history.

(56) References Cited

U.S. PATENT DOCUMENTS

| | | | |
|---|---|---|---|
| 2,214,984 | A | 9/1940 | Bachmann |
| 2,381,084 | A | 8/1945 | Slad |
| 2,894,424 | A | 7/1959 | Vaughan, Jr. |
| 3,189,374 | A | 6/1965 | Mertes |
| 3,399,583 | A | 9/1968 | Lance |
| 3,465,621 | A | 9/1969 | Ladd |
| 3,643,663 | A | 2/1972 | Sutter |
| 3,694,015 | A | 9/1972 | Gley |
| 3,699,632 | A | 10/1972 | Anhalt |
| 3,819,282 | A | 6/1974 | Schultz |
| 3,913,586 | A | 10/1975 | Baumgarten |
| 4,215,884 | A | 8/1980 | Little |
| 4,318,313 | A | 3/1982 | Tartaglia |
| 4,449,022 | A | 5/1984 | Uno et al. |
| 4,483,562 | A * | 11/1984 | Schoolman ............ A61B 17/29 606/174 |
| 4,494,543 | A | 1/1985 | Hart |
| 4,792,165 | A | 12/1988 | Nishimura |
| 5,104,397 | A | 4/1992 | Vasconcelos et al. |
| 5,176,702 | A | 1/1993 | Bales et al. |
| 5,211,655 | A | 5/1993 | Hasson |
| 5,358,292 | A | 10/1994 | Van Wiebe et al. |
| 5,425,743 | A | 6/1995 | Nicholas |
| 5,498,039 | A | 3/1996 | Bivens |
| 5,499,998 | A | 3/1996 | Meade |
| 5,735,849 | A | 4/1998 | Baden et al. |
| 5,884,954 | A | 3/1999 | Trozera |
| 6,050,996 | A | 4/2000 | Schmaltz et al. |
| 6,056,333 | A | 5/2000 | Wach |
| 6,247,733 | B1 | 6/2001 | Weiland |
| 6,254,623 | B1 | 7/2001 | Haibel, Jr. et al. |
| 6,585,735 | B1 | 7/2003 | Frazier et al. |
| 6,669,250 | B1 | 12/2003 | St. Louis |
| 6,799,705 | B1 | 10/2004 | Lutoslawski |
| 7,115,139 | B2 | 10/2006 | Mcclurken et al. |
| 7,118,587 | B2 | 10/2006 | Dycus et al. |
| 7,150,749 | B2 | 12/2006 | Dycus et al. |
| 7,201,411 | B2 | 4/2007 | Bella et al. |
| 7,232,440 | B2 | 6/2007 | Dumbauld et al. |
| 7,766,910 | B2 | 8/2010 | Hixson et al. |
| 7,793,995 | B2 | 9/2010 | King et al. |
| 7,802,856 | B2 | 9/2010 | Hashemi et al. |
| 8,109,582 | B2 | 2/2012 | Dubach |
| 8,246,094 | B2 | 8/2012 | Long et al. |
| 8,328,170 | B2 | 12/2012 | Wasinger |
| 8,398,620 | B2 | 3/2013 | Bacher et al. |
| 8,945,175 | B2 | 2/2015 | Twomey |
| 9,452,011 | B2 | 9/2016 | Batchelor et al. |
| 9,851,741 | B2 | 12/2017 | Lamser et al. |
| 10,849,641 | B2 * | 12/2020 | Boone ................ A61B 18/1447 |
| 2002/0016609 | A1 | 2/2002 | Wensel et al. |
| 2006/0190035 | A1 | 8/2006 | Hushka et al. |
| 2006/0208506 | A1 | 9/2006 | Kern et al. |
| 2008/0154300 | A1 | 6/2008 | Jabbour |
| 2011/0301637 | A1 | 12/2011 | Kerr et al. |
| 2012/0109187 | A1 | 5/2012 | Gerhardt, Jr. et al. |
| 2012/0184989 | A1 | 7/2012 | Twomey |
| 2012/0184990 | A1 | 7/2012 | Twomey |
| 2012/0191091 | A1 | 7/2012 | Allen |
| 2013/0066317 | A1 | 3/2013 | Evans et al. |
| 2013/0178852 | A1 | 7/2013 | Allen, IV et al. |
| 2013/0325057 | A1 | 12/2013 | Larson et al. |
| 2014/0135805 | A1 | 5/2014 | Windgassen et al. |
| 2014/0236156 | A1 | 8/2014 | Arlettaz et al. |
| 2014/0276795 | A1 | 9/2014 | Batchelor et al. |
| 2015/0331443 | A1 | 11/2015 | Lamser et al. |
| 2016/0051275 | A1 | 2/2016 | Batchelor et al. |
| 2016/0262826 | A1 | 9/2016 | Allen, IV |
| 2016/0338763 | A1 | 11/2016 | Allen, IV et al. |
| 2017/0367752 | A1 | 12/2017 | Boudreaux et al. |
| 2019/0298399 | A1 | 10/2019 | Boone et al. |

FOREIGN PATENT DOCUMENTS

| | | |
|---|---|---|
| CN | 107072683 A | 8/2017 |
| CN | 110313986 A | 10/2019 |
| CN | 110313986 | 7/2022 |
| CN | 115153823 A | 10/2022 |
| EP | 0392548 A1 | 10/1990 |
| EP | 0908152 A1 | 4/1999 |
| EP | 3545880 A1 | 10/2019 |
| EP | 3545880 B1 | 2/2021 |
| EP | 3858266 B1 | 8/2023 |

OTHER PUBLICATIONS

"European Application Serial No. 21156718.5, Response filed Dec. 15, 2022 to Communication Pursuant to Article 94(3) EPC dated Aug. 9, 2022", 15 pgs.

"European Application Serial No. 21156718.5, Communication Pursuant to Article 94(3) EPC dated Aug. 9, 2022", 5 pgs.

"Chinese Application Serial No. 201910171697.1, Office Action dated Dec. 2, 2021", w/ English Translation, 21 pgs.

"Chinese Application Serial No. 201910171697.1, Response Filed Feb. 17, 2022 to Office Action dated Dec. 2, 2021", with machine translation, 12 pgs.

"Chinese Application Serial No. 201910171697.1, Response filed Mar. 30, 2022", with English claims and machine translation, 12 pgs.

"European Application Serial No. 21156718.5, Response filed Jan. 21, 2022 Extended European Search Report dated Jun. 10, 2021", 83 pgs.

"U.S. Appl. No. 15/941,205, Non Final Office Action dated Jan. 27, 2020", 15 pgs.

"U.S. Appl. No. 15/941,205, Notice of Allowance dated Jun. 12, 2020", 9 pgs.

"U.S. Appl. No. 15/941,205, Notice of Allowance dated Jul. 31, 2020", 10 pgs.

"U.S. Appl. No. 15/941,205, Response filed Apr. 27, 2020 to Non Final Office Action dated Jan. 27, 2020", 16 pgs.

"U.S. Appl. No. 15/941,205, Response filed Nov. 26, 2019 to Restriction Requirement dated Oct. 10, 2019", 7 pgs.

"U.S. Appl. No. 15/941,205, Restriction Requirement dated Oct. 10, 2019", 6 pgs.

"Closure Assembly That is Laterally Movable for Selective Locking", Potentially related U.S. Appl. No. 15/941,128, filed Mar. 30, 2018, 39 pgs.

(56) References Cited

OTHER PUBLICATIONS

"Endoscopic Cutting Forceps With Jaw Clamp Lever Latching Mechanism", Potentially related U.S. Appl. No. 14/706,146, filed May 7, 2015, 40 pgs.

"European Application Serial No. 19164182.8, Extended European Search Report dated Aug. 23, 2019", 7 pgs.

"European Application Serial No. 19164182.8, Response filed Mar. 26, 2020 to Extended European Search Report dated Aug. 23, 2019", 8 pgs.

"Forceps Including a Double Biased Handle Latch", Potentially related U.S. Appl. No. 15/941,590, filed Mar. 30, 2018, 48 pgs.

"Forceps Including a Pre-Loaded Handle Latch", Potentially related U.S. Appl. No. 15/967,491, filed Apr. 30, 2018, 40 pgs.

"Halo Cutting Forceps", Olympus, [Online] Retrieved from the internet: <http://www.olympusamerica.com/msg_section/envision/oneoffpages/files/Halo_PKS_Brochure.pdf> (Last Accessed May 14, 2018), (Apr. 3, 2014), 2 pgs.

\* cited by examiner

FORCEPS INCLUDING A PRE-LOADED HANDLE LATCH

CROSS-REFERENCE TO RELATED APPLICATION

This application is a Continuation of U.S. patent application Ser. No. 15/941,205, filed Mar. 30, 2018 and issued on Dec. 1, 2020 as U.S. Pat. No. 10,849,641, the contents of which are hereby incorporated by reference in their entirety.

FIELD

The present teachings relate to forceps with a first jaw and a second jaw that are movable relative to each other and the forceps include a movement unit and a latch unit that when connected prevent movement of the first jaw to the second jaw, and specifically a latch unit that includes a compression spring, which is pre-loaded so that the compression spring provides a force upon the movement unit when the movement unit and/or the latch unit are in a home position.

BACKGROUND

Generally, forceps may be utilized for laparoscopic surgery or open surgery. The forceps may be used to control delicate movements inside a patient. These forceps may be used to grip an anatomical feature. The forceps may include a gripping assembly or a cutting assembly. The forceps may include electrical energy for use in the gripping assembly, the cutting assembly, or both. The forceps have a pair of opposed resilient jaws that are closed against each other or a cutting blade. The jaws of the forceps may be locked together so that the surgeon may lock the forceps on a feature of interest while the surgeon works on a different anatomical feature or uses a different instrument. Examples of some latches or forceps including locks may be found in U.S. Pat. Nos. 5,104,397; 6,056,333; 6,247,733; 7,802,856; and 8,945,175 and U.S. Patent Application Publication No.: 2013/0066317; 2014/0276795; 2015/0331443; 2016/0051275 all of which are incorporated by reference herein in their entirety for all purposes. During locking of the arms to each other the user may have to regrip one or more times in order to lock the jaws together. Furthermore, during releasing the user may be required to manipulate the jaws one or more times in order for the lock to release the jaws.

It would be attractive for the forceps to include one or more springs that are pre-compressed so that a bias force acts upon a latch unit so that the latch unit creates positive positioning as a bar extends into and out of the latch unit. What is needed is a latch unit that is positively biased so that as the latch unit assists in locking a portion of a movement unit in place during a locking action and releasing a portion of the movement unit upon a releasing action. What is needed is a latch plate including a hook latch that is movable with the latch plate and a rear post and a forward post that pre-compress a bias member therebetween so that movement of the latch plate either increases a bias force created by the bias member or decreases a bias force created by the bias member. It would be attractive to have a bias member that is pre-compressed and exerts a bias force when in a home position, a locking position, or an unlocking position.

SUMMARY

The disclosure meets one or more of the needs by providing: a closure assembly comprising a latch unit and a movement unit. The movement unit is connected to a movable member that moves along a prescribed path. The latch unit is connected to a ground member and the latch unit is movable relative to the ground member. The latch unit includes a bias member that is pre-loaded when the bias member is located within the latch unit and the latch unit is located in a home position. The bias member increases in a load relative to the pre-load when the latch unit is moved in the first direction away from the home position and the second direction away from the home position.

The present teachings provide a surgical device comprising: a closure assembly including: (a) a latch unit comprising: (A) a hook latch, having a home position. (B) a forward bias constraint. (C) a rearward bias constraint, and (D) a bias member extending between the forward bias constraint and the rearward bias constraint so that the bias member has a pre-load when the hook latch is in the home position; (b) a movement unit including a bar that is movable relative to the latch unit so that the bar is movable in a prescribed motion into contact with the latch unit to create a locked state; and wherein the bar moves into contact with the hook latch driving the hook latch in a first direction, away relative to the home position, and then the hook latch is moved by the bar in a second direction relative to the home position, and a loading of the bias member is increased from the pre-load when the hook latch is moved in either the first direction away from the home position or the second direction away from the home position.

The teachings herein provide forceps to include one or more springs that are pre-compressed so that a bias force acts upon a latch unit so that the latch unit creates positive positioning as a bar extends into and out of the latch unit. The teachings herein provide a latch unit that is positively biased so that as the latch unit assists in locking a portion of a movement unit in place during a locking action and releasing a portion of the movement unit upon a releasing action. The teachings herein provide a latch plate including a hook latch that is movable with the latch plate and a rear post and a forward post that pre-compress a bias member therebetween so that movement of the latch plate either increases a bias force created by the bias member or decreases a bias force created by the bias member. The teachings herein provide a bias member that is pre-compressed and exerts a bias force when in a home position, a locking position, or an unlocking position.

BRIEF DESCRIPTION OF THE DRAWINGS

FIG. 38 is a close-up view of a movement unit and a latch unit in an unlockable state with a portion the selection plate removed from the latch unit;

DETAILED DESCRIPTION

Figure 1:
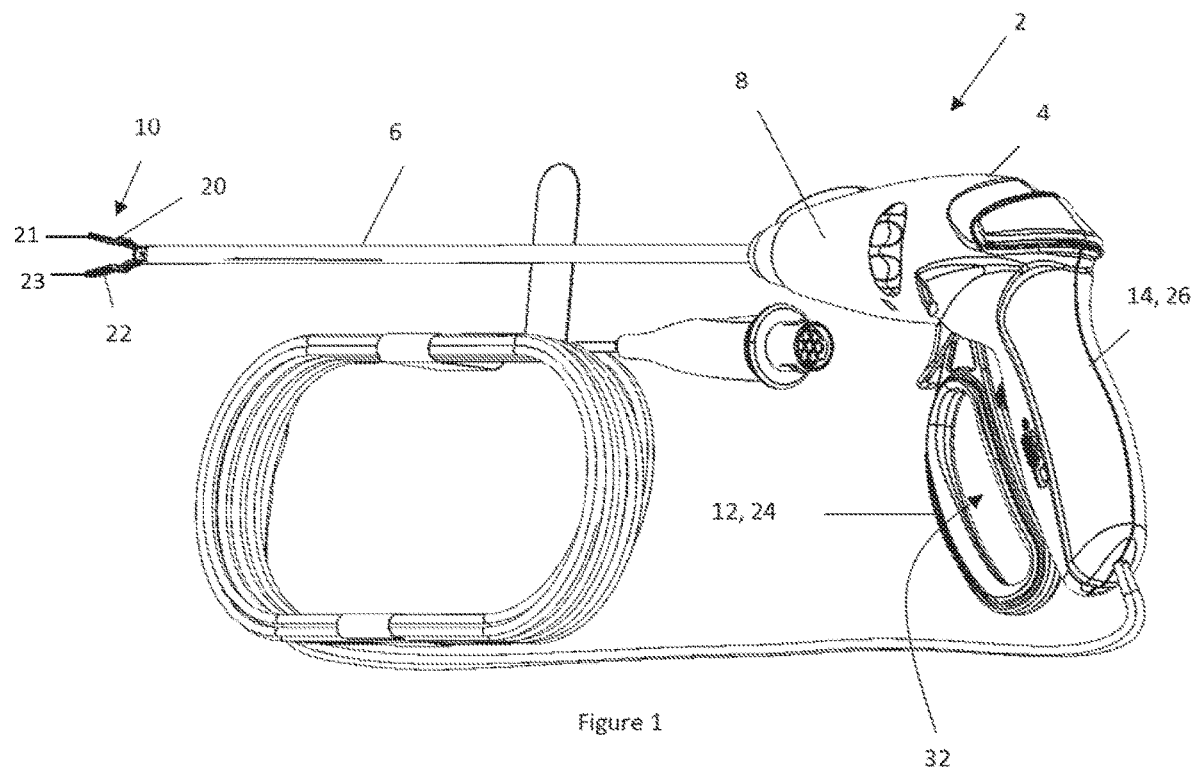
FIG. 1 is a perspective view of an electrosurgical device having a latching assembly.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present teachings relate to a closure assembly that connects two or more members together and prevents movement of the two members relative to each other. The closure assembly may connect a movable member to a ground member or connect two movable members together. The closure assembly may prevent movement of a door (e.g., movable member) relative to storage space (e.g., ground member). The closure assembly may be part of a hand-held device, pliers, clamps, or a combination thereof. The closure assembly may be part of a drawer, cabinet, bin, a door, or a combination thereof. Preferably, the closure assembly is part of a surgical device and prevents arms that control forceps from moving relative to each other.

The present teachings relate to a surgical device. The surgical device may be a non-electrical device (i.e., may only provide mechanical functions such as mechanical cutting or gripping). Preferably, the surgical device is an electrosurgical device. The electrosurgical device may provide one or more therapy currents. Preferably, the electrosurgical device provides two or more therapy currents (e.g., monopolar power and bipolar power). A therapy current may pass between the jaws (e.g., bipolar power). A therapy current may pass from a jaw to a blade or vice versa. A therapy current (e.g., monopolar power) may pass from a blade to a remote electrode (e.g., ground pad). The electrosurgical device may apply power before, after, or simultaneously with a mechanical technique (e.g., gripping or cutting). When power is applied an anatomical feature may be cut, cauterized, sealed, coagulated, or a combination thereof. The electrosurgical device may include a distal end and a proximal end. The distal end may include a portion of a forceps device (e.g., jaws, blade, or both). The distal end may be a portion of the surgical device that is farthest from a user. The proximal end may be a portion a user grips (e.g., hand piece or housing) or a portion closest to a user.

The present teachings provide a forceps device. The forceps may function to grip an object. Preferably, the forceps may be used during surgery to grip a feature of interest including: a part of a body, an anatomical feature, tissue, veins, arteries, or a combination thereof. The forceps may assist in applying a therapy current to a feature of interest. The forceps may move between a first position (e.g., release position) and a second position (e.g., gripping position). The forceps may be fully closed in a full-pull position or partially closed in a partial pull position. The forceps may function to be used in surgery, for example laparoscopic surgery. The forceps may be used with or without power. A therapy current may be passed from one jaw to a second jaw when tissue is located between the jaws and the therapy current may coagulate blood, cauterize, cut, or a combination thereof. In another example, a therapy current may be passed from one or more of the jaws and/or a blade to a remote electrode (e.g., a return pad). The forceps may include a first working arm with a jaw and a second working arm with a jaw. The forceps may be comprised of parts needed to perform the recited functions and may include generally, a stylet (e.g., a tubular member, a hollow tube, or an assembly of tubes), a hand piece, one or more operable mechanisms used to actuate the stylet, two or more jaws, two or more working arms, or a combination thereof.

The two or more working arms may function to move towards and away from each other to assist a user in gripping a feature of interest. The two or more working arms may be directly biased towards each other by a user. Preferably, the two or more working arms are biased towards each other by a stylet or tube moving over the arms (e.g., distally) so that the arms are moved together. The two or more working arms may be moved towards each other by being retracted into a stylet or tube. The working arms may be solid and rotate about a pivot. The working arms may be a wire that is shaped to create a working arm, a jaw, or both. The working arms may have one or more rods, one or more wires, or both that extend into a stylet and connect to the hand piece. Each of the two or more working arms may include a jaw.

The two or more opposing jaws may function to create a gripping force, grip a feature of interest, or both. The two or more opposing jaws may move towards each other to create a gripping force, to grip a feature of interest, or both. The two or more opposing jaws may function to be used to grip or clamp an item of interest for cutting or applying a bipolar energy source. Preferably, the two or more opposing jaws may be one jaw structure with another mirror image opposing jaw structure (i.e., identical) that when forced together may create a gripping function. The two opposing jaws may be any two or more structures that may be movable relative to each other for perform a gripping function. The two opposing jaws may be any structures that may allow one jaw to be static and one jaw to be movable or any combination thereof. The jaws may be a gripping portion of a working arm. The two opposing jaws may be formed of two wires that are shaped to have a generally U shaped end. The two opposing jaws may be made of any material so that the two opposing jaws may be used to create a gripping force. The two opposing jaws may be made of a flexible material, resilient material, rigid stainless steel, a plastically deformable material, an elastically deformable material, or a combination thereof. The two opposing jaws may be made of a material that conducts electricity. The two opposing jaws may include a channel (e.g., a blade track) to allow for a cutting instrument to be inserted while retaining functionality of the two or more opposing jaws.

The two opposing jaws may be used to apply electricity to a feature of interest that may be gripped by the two opposing jaws. The two opposing jaws may be a first jaw and a second jaw. The first jaw may be movable relative to the second jaw, or vice versa. The first jaw and second jaw may be longitudinally movable relative to each other. Preferably, the first jaw and second jaw longitudinally move in unison. The first jaw and second jaw may be longitudinally static. The first jaw and second jaw may move about a pivot towards and away from each other. The two opposing jaws may be moved between a release position and a retract position by retraction of one of the one or more jaw shafts, movement of the one or more tubular members towards the distal end, or both along an axis of the one or more tubular members; an application of force by a user; or a combination thereof. The two opposing jaws may have laterally extending arcuate sections at the proximal end (e.g., heel of the jaw) of the jaws that protrude out from the distal end of the tubular member, while one or more jaw support rods extend into the tubular member. A closure assembly may lock the two opposing jaws together, lock the two opposing jaws on tissue, lock the two opposing jaws on a blade, or a combination thereof.

The blade may function to cut a feature of interest. The blade may be any cutting tool that may be used in surgery, for example laparoscopic surgery or open surgery. The blade may be any cutting device that may be extended and retracted through the stylet. The blade may extend along a stylet. The blade may be made of any material that may be sharpened; is strong enough to cut a feature of interest: is biocompatible; that may conduct electricity; or a combination thereof. The blade may mechanically cut, electrically cut, or both. The blade may be substantially solid along a length of the blade. The blade may be sufficiently small so that the blade may be housed in the tubular member, tube, or both of a stylet during movement, insertion, or both. The blade may be extended into, and retracted from, the channel in the two opposing jaws. The distal end of the blade may have a shaped edge (e.g., sharpened). The blade may extend flush with or distal of the jaws. The blade may conduct power. The blade may conduct a therapy current. The blade may conduct bipolar energy, monopolar energy, or both. The proximal end of the blade may be attached to a blade support rod. All or a portion of the blade may extend out of the stylet between and past the jaws to cut a feature of interest.

The stylet as discussed herein may include one or more tubular members or may be a tubular member (i.e., tube). The stylet may be a neck that connects jaws, a blade, or both to a hand piece. The stylet may have a hollow cross-section, a solid cross-section, or both. The stylet may include one or more tubes, one or more shafts, or both that may extend through the tubes. For example, an inner tube may be solid and an outer tube may be hollow. The stylet may include a tubular member and an inner tube. The stylet may include a tube that extends around all or a portion of an inner tube. The stylet may be a hollow tube with one or more shafts extending through the hollow tube. The stylet may function to extend into a patient during a surgical procedure so that a user (i.e., surgeon) can perform one or more surgical procedures. The stylet may be flexible so that the stylet may be moved within a patient. Preferably, the stylet may be substantially rigid so that the stylet may be moved to a desired location. The stylet includes a distal end and a proximal end. The distal end may be an end of the stylet that is located farthest from the hand piece (e.g., the end of the stylet that is inserted into a patient). The proximal end of the stylet may be the end of the tube located proximate to the user, in the hand piece, or both. The stylet and its components may be made of any biocompatible material, for example, stainless steel, plastic, a synthetic material, a natural material, or a combination thereof. The tube subassembly may include one or more tubes, one or more inner tubes, one or more outer tubes, one or more gripping assemblies, one or more cutting assemblies, one or more rotation mechanisms, one or more operable mechanisms, one or more camming shafts, one or more guides, one or more spacing members, one or more jaw shafts, one or more blade shafts, or a combination thereof. Preferably, the stylet includes at least an outer tube that extend from a hand piece to a distal end.

The one or more outer tubes may function to close the jaws, bias the jaws, or both. The one or more outer tubes may function to house one or more jaws, one or more blades, or both. The one or more outer tubes may be axially static. The one or more outer tubes may axially move to open and close the jaws. The one or more jaws may move relative to the inner tube. The one or more jaws may axially move towards the distal end and the proximal end during movement. The one or more jaws may overrun the inner tube, the jaws, the arcuate sections, or a combination thereof to bias the jaws towards each other. The one or more inner tubes may function to create a point of contact for one or more jaws. The one or more inner tubes may form a connection point, include a connection feature (e.g., a pin, bolt, screw, rivet, or a combination thereof) for one or more jaws. The one or more inner tubes may connect to a pivot joint of one or more jaws so that the one or more jaws rotate about an axis. The one or more inner tubes may assist in opening and closing the jaws. The one or more inner tubes may be located distal of one or more tubes. The one or more inner tubes may be part of a tubular member or a stylet. The one or more inner tubes may be movable relative to an outer tube. The one or more inner tubes may be axially movable, rotationally movable, or both relative to an outer tube, a camming shaft, or both. The one or more inner tubes may be static and an outer tube may be movable relative to the inner tube. The one or more inner tubes may be substantially the same length as an outer tube. The one or more inner tubes may be shorter than an outer tube. The one or more inner tubes may be hollow. The one or more inner tubes may be solid. The one or more forceps may be free of any tubes or tubular members. The one or more inner tubes, outer tubes, stylets, or a combination thereof may form part of a fluid distribution system, connect a fluid distribution system between a jaw, blade, or both and a hand piece. The one outer tubes of the stylet may assist in connecting the jaws, the blade, or both to the hand piece.

The hand piece may be an assembly of parts or housing structures capable of forming a structure with a cavity that a user holds in their hand. The hand piece may function to be gripped by a user. When gripped by a user a top or upper portion of the handpiece may be located up relative to a user's hand and the bottom or lower portion may be located down relative to a user's hand. Thus, up may include the one or more button, a region the stylet extends from, or both, and down may be where a cord extends out of the hand piece. The hand piece may function to hold or encapsulate one or more or a plurality of components of the surgical device. The forceps may extend from the hand piece and may be actuated by one or more operable mechanisms located within the hand piece. The forceps may be actuated by movement of a trigger that is connected to the hand piece. The hand piece and the trigger may be biased apart. A bias device may extend between the hand piece and the trigger so that a gap is located between the hand piece and the trigger. A bias device may be located along the stylet, within the hand piece, in communication with a part that axially moves so that the working arms are moved together, or a combination thereof. The bias device may be a bias device taught herein including those taught in U.S. Pat. No. 9,851,741 regarding a compression spring or element 90 or the teachings of U.S. Pat. No. 5,735,849 regarding a torsion spring or element 80 the teachings of which are incorporated by reference herein for all purposes include those regarding how a moveable member is moved relative to a ground member and especially how a trigger is moved relative to a handle. The hand piece may include the latch unit and the trigger may include the movement unit and when the movement unit and the latch unit are not connected together the bias member may move the trigger to form the gap therebetween. The forceps may create a sufficient gripping force so that one or more features of interest of a patient's body may be manipulated by the gripping assembly, secured by the gripping assembly, or a combination thereof. The forceps may be an assembly of parts rotatable about an axis (e.g., a rotational axis of the forceps, the longitudinal axis of the tubular member, a longitudinal axis of the forceps, or a combination thereof) relative to the hand piece. The forceps may grip and release while being simultaneously rotated about the hand piece. The forceps may be actuated by the actuation mechanism in communication with the forceps or a user directly contacting the forceps. The hand piece may function to form an enclosing structure for all or a portion of the forceps, a gripping portion for the user, a main portion for manipulating the forceps, or a combination thereof. The hand piece may be any device that houses all or a portion of the working assemblies and parts of the forceps. The hand piece may be comprised of one or more housing structures. Preferably, the hand piece is two or more housing structures. The housing structures may be two plastic pieces that connect together to enclose an open space that receives components of the surgical device. The hand piece may be any structure that is gripped by a user. The hand piece may be a ground member. The hand piece may be static. The hand piece may be a ground member that is static when a user applies a pressure to so that a movable member is moved relative to the ground member. The hand piece may be gripped by a user during a procedure. The hand piece may be any structure that combines one or more of the components discussed herein so that the surgical device is formed. The hand piece may assist in performing laparoscopic surgery. The hand piece may be ergonomically shaped. The ergonomic shape of the hand piece may be any shape so that the forceps may be used ambidextrously. The ergonomic shape of the hand piece may be any shape such that all the controls can be accessed by a single hand gripping the hand piece. The hand piece may be comprised of housing structures. The housing structures may be any devices that may affix certain pieces into position. The housing structures may form a cavity to house working assemblies of the forceps. The housing structures may be one or more housing structures and preferably two or more housing structures. The housing structures may be any device that includes a recess for receiving one or more components of the forceps. The housing structures may house all or a portion of one or more operable mechanisms, one or more valves, one or more fluid distribution systems, or a combination thereof. The housing structure may house all or a portion of an operable mechanism that causes the jaws to move, the blade to move, the valve to open, the valve to close, all or a portion of a fluid distribution system, or a combination thereof. The housing structure may be made of one or more housings.

The one or more housings may function to form a hand piece, enclose a portion of an operable mechanism, enclose a portion of a stylet, enclose one or more tubes, or a combination thereof. The one or more housings may be a left half and a right half. The housing may be multiple pieces that are connected together. The housing may be made of plastic. The housing may be a combination of plastic and metal. The housing may include a grip. The housing may be a handle that a user grips. The housing may provide a stationary part (e.g., ground member) that a user grips while a user moves a trigger (e.g., movable member) to actuate the forceps, a blade, or both. Preferably, the housing is connected to two or more triggers that movably connect to the housing so that upon actuation the jaws, blade, fluid distribution system, or a combination thereof are moved or actuated by one of the two or more triggers. More preferably, the triggers are movable relative to the housing to actuate the jaws, blade, fluid distribution system, or a combination thereof. The housing may be connected to a first jaw, a second jaw, or both jaws of forceps and a direct force may be applied to the housings in order to move the forceps towards or apart from each other. For example, upon a force being applied to the housing the jaws may move towards each other. In another example, upon a force being applied to the housing the jaws may move apart. The housing may be a proximal end (e.g., end closest to a user) and the jaws or blade may be the distal end (e.g., end farthest from a user). However, the housing may extend from a proximal end to substantially the distal end. The jaws, blade, fluid distribution system, or a combination thereof may be moved between a first position (release position) and a second position (retract position) by one or more operable mechanism or direct contact by a user. The housing may have a portion that is a handle that a user grips.

The handle may function to assist in actuation of the forceps, the blade, applying electricity, or a combination thereof. The handle may be gripped by one hand. The handle may be part of the hand piece. The handle may include a lock, a lock plate, all or a portion of a closure assembly, a latch unit, or a combination thereof. The handle may be a proximal end of the surgical device. The handle may extend from a body portion or the hand piece. The handle may extend from an angle relative to the body portion. The handle may be a static member that one or more triggers move relative to. The handle may be a ground member that a movable member, a trigger, or both are movable relative to.

The ground member may function to be a movable member or a static member that another part (e.g., the movable member) is moved relative to. The ground member may be a central component fora coordinate system or a reference point for relative motion of other components of the device taught herein. The ground member may be connected to or located next to a movable member and function to prevent movement of another component such as forceps or a blade as the movable member moves relative to the ground member. The ground member may be part of a first working arm. The ground member may be a handle, a housing, a hand piece, a trigger, a jaw, or a combination thereof. The ground member may include all or a portion of a closure assembly. The ground member may include all of the latch unit. The ground member may receive a portion of a force to assist a movable member in being moved relative to the ground member. The ground member may receive a portion of the movable member to form a locked state.

The movable member may function to move relative to a ground member so that the forceps may be actuated, locked, released, or a combination thereof. The movable member may be biased apart from the ground member (e.g., a bias device may be located between the movable member and the ground member). The movable member may move with or relative to an ground member to lock, unlock, bias, or a combination thereof two or more jaws or two or more working arms. The movable member may move to open and close the jaws, move the blade, or both. The movable member may be a trigger. The movable member may include all or a portion of the closure assembly. The movable member may include the movement unit. The movable member may rotate about a pivot so that the movement unit moves along movement path (e.g., prescribed motion). The movable member may be part of the closure assembly that assists in locking the jaws, the working arms, the surgical device, or a combination thereof.

The closure assembly may function to connect a movable member and an ground member together. The closure assembly may function to lock a first working arm to a second working arm, a first jaw to a second jaw, or both. The closure assembly may be movable between a lockable state and an unlockable state. The closure assembly may lock two items together when the closure assembly is in a locked state. The closure assembly may freely move as the movable member, the ground member, or both move relative to each other or are in an unlockable state. A portion of the closure assembly may be located on or within the movable member, the ground member, the movement unit, the latch unit, or a combination thereof. Preferably, the closure assembly includes a movement unit and a latch unit. More preferably, the closure assembly may be part of a movable member and the movable member may be a trigger.

The one or more triggers function to be an input to an operable mechanism that moves one or both jaws, one or both working arms, or both. The one or more triggers may be a movable member or a ground member. Preferably, the triggers are a movable member and the ground is a handle or hand piece. The one or more triggers as discussed herein may be a lever, handle, link, or a combination thereof. The one or more triggers may be a cut trigger, a clamp trigger, an activation switch, or a combination thereof that when actuated inputs movement into an operable mechanism so that the operable mechanism provides an output. If the triggers are a lever, the lever is a rigid member that turns on a pivot. The cut lever, the clamp lever, or both may function to move one or more jaws, one or more blades, a jaw support rod, a blade support rod, a second link, one or more valves, or a combination thereof. The cut lever, the clamp lever, or both may extend between a release position (e.g., a start position) and a retract position (e.g., a full pull position where the jaws are closed, the blade is extended, or both). The cut lever and the clamp lever may be individually biased apart from the handle, the hand piece, or both. The cut lever, the clamp lever, or both as they extend from a start position to a full pull-position (e.g., a forward stroke) may close jaws, activate a functional element, extend a blade, or a combination thereof. For example, as the clamp trigger moves in a forward stroke, the clamp trigger may begin to close the jaws and as the jaws close a closure assembly may simultaneously be closed such that the jaws are locked together. The one or more triggers may be part of the closure assembly, part of a movement unit, or both. Preferably, the one or more triggers carry the movement unit so that the movement unit when in communication with the latch unit may restrict movement of the trigger.

The movement unit may be integrally connected to a movable member, a trigger, or both. The movement unit may extend from the movable member towards the ground member and even into the ground member. The movement unit may move in a prescribed motion. The prescribed motion may be a forward stroke and a return stroke. The forward stroke may be the movement member extending towards the ground member and the return stroke may be the movement member extending away from the ground member. The prescribed movement may be a linear motion, an arcuate movement, or a combination of both. The prescribed motion may overlap in a first direction and a second direction. The movement unit may rotate about a pivot so that the movement unit travels back and forth along a constant path (e.g., a prescribed motion). The movement unit may extend cantilevered from a movable member, a trigger, or both. The movement unit may extend into contact with a latch unit to form a locked state. The movement unit may move in relationship to the latch unit to form an unlocked state. The movement unit may move in a prescribed motion at all times and the latch unit may move relative to the movement unit so that a lockable state, an unlockable state, a locked state, an unlocked state, or a combination thereof may be formed. The movement unit may include one or more bar arms, one or more bars, or both.

The one or more bar arms may function to extend from a movable member so that a portion of the bar arm, the bar, or a combination thereof are extendable into a ground member, a latch unit, or both. The one or more bar arms may extend cantilevered from the trigger, the movable member, or both. The one or more bar arms may extend partially into the latch unit, a latching pathway, around a hook latch, or a combination thereof. The one or more bar arms may be located at virtually any location on a movable member, a trigger, or both. Preferably, the one or more bar arms are located on a bottom of the movable member. The one or more bar arms may be linear in shape. The one or more bar arms may be tapered. The one or more bar arms may taper as the bar arms extend away from the movable member and towards the ground member. The one or more bar arms may taper in shape so that once a sufficient amount of the bar arm extends into the latch unit, the latching pathway, or both the one or more bar arms may be prevented from extending further into the latch unit, the latching pathway, or both. A distal end, narrowest region, tapered portion, end that extends into the latch unit, end that extends into the latching pathway, or a combination thereof may include one or more bars. Preferably, the one or more bars may be located on a side of the bar arm. More preferably, the one or more bars extend substantially normal from the bar arm.

The one or more bars may function to connect the movement unit to the latch unit so that movement of the movable member relative to the ground member is prevented (e.g., create a locked state). The one or more bars may move through a pathway in a forward stroke to connect to the latch unit and then move through the pathway in a return stroke to release or move away from the latch unit. The one or more bars may be virtually any shape so that the bars are movable through a latching pathway into the latch unit and then along a pathway to create a locked state and an unlocked state. The one or more bars may contact a hook latch to create a locked state. The one or more bars may be moved away from a hook latch to move along the pathway from a locked state to an unlocked state (e.g., a return stroke). The one or more bars may only extend along one side of the hook latch. Preferably, the one or more bars may circumnavigate the hook latch. The one or more bars may be a projection that extends from the bar arm and ultimately from a movable member or a trigger so that when the bar is trapped the movable member, the trigger, or both are prevented from being moved. The bar may be cylindrical, cubical, a cone, a cuboid, or a combination thereof. Preferably, the bar is cylindrical so that the bar may extend through a latching pathway, into the latch unit, and around a pathway of the latch unit.

The latching pathway may function to receive the bar into the latch unit the ground member, the housing, the handpiece, the handle, or a combination thereof. The latching pathway may be an opening in the housing, hand piece, forceps, handle, or a combination thereof. The latching pathway is aligned within bar so that as the bar moves in a prescribed motion the bar will pass into and through the latching pathway. The latching pathway may be an absence of material. The latching pathway may be part of the housing, handle, hand piece, or a combination thereof (e.g., a gap or spaced formed in the housing). The latching pathway may permit ingress and egress of the latch unit relative to the housing, the handle, hand piece, or a combination thereof.

The latch unit may function to create a connection with a movement unit so that the movable member and the ground member are locked together. In the locked state, the bar is impeded from moving by the latch unit so that the trigger, movement member, or both cannot perform a return stroke. The latch unit may retain a portion of the movement unit. The latch unit may move as the movement unit moves along a prescribed path, an arcuate movement, or both. The latch unit may include a lockable state, an unlockable state, or both. The latch unit may be under a load (or pre-load) when the closure assembly is moved between or to a home position, a locking position, an unlocked position, a lockable state, an unlockable state, or a combination thereof. The latch unit may move along a longitudinal axis (e.g., all or a portion of the latch unit may move along the handle, the hand piece or both up and down as the movement unit moves into contact with the hook latch or out of contact with the hook latch). The latch unit may be in a pre-loaded state (e.g., a bias member may be a compression spring that is compressed) before the movement unit is in contact with the latch unit. The latch unit may be pre-loaded by a bias member being constrained between a forward bias constraint and rearward bias constraint.

The forward bias constraint may function to create one end of a constraint that places a load on a bias member so that the bias member is pre-loaded. A rearward bias constraint may function to create a second end of a constraint that places a load on a bias member so that the bias member is pre-loaded. The forward bias constraint, the rearward bias constraint, or both may be connected to the latch unit and preferably to the latch plate. The forward bias constraint and the rearward bias constraint (hereinafter bias constraints) may be connected to the latch plate and cause movement of the latch plate as the bias member is loaded and unloaded between the bias constraints. The bias constraints may form a box structure that extends along all sides of the bias member. The bias constraints may only extend along axial ends of the bias member. The bias constraints may extend along a forward end and a rear end of the bias member. The bias constraints may be a post, a wall, a contact surface, a contact surface including one or more guides, two contact surfaces that a separated by a guide, or a combination thereof. The forward bias constraint and the rearward bias constraint may be connected on a first side, a second side, or both by one or more side constraints.

The one or more side constraints may function to maintain a bias member within a plane, along an axis, all of the helical loops concentric, or a combination thereof. The one or more side constraints may prevent bowing or bending of a bias member. The one or more side constraints may contact the bias member at one or more locations. The one or more side constraints may be a wall, an extension of the forward bias constraint, the rearward bias constraint, or both. Preferably, there are two side constraints and the two side constrains are parallel. The one or more side constraints may be connected to the latch plate. The one or more side constraints may be free of contact with the forward bias constraints, the rearward bias constraints, or both. Latch plate may be free of side bias constraints. The one or more side constraints may extend parallel to a longitudinal axis of the bias member, parallel to a sliding axis of the forward movable bias constraint rearward movable bias constraint, a latch plate, or a combination thereof.

The one or more forward movable bias members, one or more rearward movable bias constraints, or both (hereinafter movable bias constraint) may function to change a load on a bias member that is pre-loaded between two bias constraints. The movable bias constraints may move relative to the bias constraints, the latch plate, or both. The movable bias constraints may move between a lockable state and an unlockable state. The movable bias constraints may change a load of the bias member as the latch plate moves along a sliding axis. The movable bias constraint when in a lockable position may be positioned so that as the latch plate moves along the sliding axis the load on the bias member is increased. The movable bias members may increase a load in the bias member when the latch plate moves in a first direction (e.g., rearward), in a second direction (e.g., forward), or both. Preferably, the movable bias members increase a load on the bias member, relative to the pre-load, when the latch plate moves in the first direction and the second direction. The forward movable bias member may be located at a forward end, proximate to a forward bias member, or both. The rearward movable bias member may be located at a rearward end, a rearward bias member, or both. The movable bias members may be a post, a wall, a contact surface, a contact surface including one or more guides, two contact surfaces that a separated by a guide, or a combination thereof.

The rear post and the forward post may function to pre-load a bias member. The rear post and forward post may be substantially aligned and a bias member may extend therebetween. The rear post and the forward post may be static relative to each other, the hook latch, the handle, the housing, the hand piece, or a combination thereof. The rear post and forward post may be movable relative to the housing, the handle, the hook latch, the hand piece, or a combination thereof. The rear post and the forward post may be movable between a lockable state and an unlockable state. The rear post and the forward post may contact a bias member and constrain the bias member therebetween to form a pre-load. The rear post and the forward post may receive a portion of the bias member so that the bias member is constrained relative to the rear post, the forward post, or both. The rear post, the forward post, or both may move with the latch plate or the rear post or the forward post may contact the bias member and increase a load on the bias member relative to the pre-load when the rear post, forward post, or both move relative to the latch plate. The rear post, the forward post, or both may be connected to a latch plate.

The rear post and the forward post may both be connected to a selection plate. The rear post, the forward post, or both may extend cantilever from the latch plate or the selection plate. The rear post, the forward post, or both may be located at an end of a latch plate or selection plate. Preferably, the rear post is located at an end and the forward post is located in a central region of the latch plate or selection plate. The rear post, the forward post, or both may have a cross-sectional thickness, height, or both that is less than that of the bias member so that the bias member extends beyond one or more sides of the rear post, the forward post, or both. For example, the post may be 1 mm wide and the bias member may be 2 mm wide and 0.5 mm may extend beyond each side of the post so that the bias member may be contacted by rear guide, a forward guide, one or more contact surfaces, or a combination thereof during movement of the latch plate while the bias member remains in contact with and connected to both the rear post and the forward post. The rear post, the forward post, or both may have a length that is longer than a cross-sectional length of the bias member. The rear post and the forward post may be located a distance apart. The distance between the rear post and the forward post may be substantially equal to the distance between the forward contact surface and the rearward contact surface (e.g., within about 5 mm or less, about 3 mm or less, or about 1 mm or less). A contact surface may be located on each side of the rear post, the forward post, or both and the rear post, the forward post, or both may extend between the one or more contact surfaces and the bias member may contact the contact surfaces. The rear post, the forward post, or both may be a contact surface that contacts the bias member when the rear post, the forward post, or both are connected to the selection plate. The rear post, the forward post, or both may be movable with the latch plate and may extend through a rear guide, a forward guide, or both respectively as the latch plate moves. The rear post, the forward post, or both may be static and the rear contact surface including a rear guide, a forward contact surface including a forward guide, or both may move to receive a rear post or a forward post respectively to bias the bias member. The rear post and the forward post may be complementary to each other, mirror images, or both. The rear post, the forward post, or both may taper from a base (e.g., a portion connected to the latch plate or the selection plate) toward a top end. A base of the rear post and the forward post may contact the bias member. A top end of the rear post, the forward post, or both may extend away from the bias member and a base of the rear contact surface, the forward contact surface, or both may contact the bias member so that the top end of the rear post, the forward post, or both may be free of contact with the bias member. The taper of the rear post, the forward post, or both may extend at an angle of about 10 degrees or less, preferably about 5 degrees or less, or about 3 degrees or less relative to a line or plane normal to a surface of the latch plate or the selection plate. The taper of the rear post, the forward post, or both may extend at an angle of about 0.5 degrees or more, about 1 degree or more, or about 2 degrees or more relative to a line or plane normal to a surface of the latch plate or the selection plate. An angle of taper of the posts may math an angle of taper of a respective contact surface so that a bias member is equally constrained therebetween when the latch unit is in a home position or a neutral position (e.g., where only the pre-load is being applied). Thus, the rear post, the forward post, or both may assist in creating the pre-load when connected to the selection plate, or the latch plate. The rear post, the forward post, or both may include a crossbar (e.g., a rear crossbar or a forward cross bar) that extend from the respective post to assist in connecting the respective post to the bias member. The rear post, the forward post, or both may be free of a cross bar.

The forward crossbar and rearward crossbar (hereinafter crossbar) function to assist in retaining the bias member in communication with the forward post and the rearward post (hereinafter post) respectively as the bias member compresses and decompresses. The crossbars may extend normal from the posts. The crossbars may form a cantilever connection with the posts. The crossbars may extend into the bias member. The crossbars may only be present when the cross bars are part of the latch plate. The crossbars may extend around a portion of the bias member. The crossbars may have a piece that extends in a single plane. Preferably, the crossbars include two perpendicularly intersecting members that are connected together. The crossbars may have a cross-sectional shape that is "+" shaped, "t" shaped, "x" shaped, or a combination thereof. The crossbars may be symmetrical. The crossbars may be asymmetrical. The crossbars may include a tapered end. The crossbars may taper to a point. The rearward crossbar may point towards the forward crossbar. The bias member may move along the rearward crossbar and the forward crossbar as the bias member moves into contact with or out of contact with the rear guide, the forward guide, or both (herein after the guides).

The guides may function to compress the bias member as the bias member moves along the longitudinal axis, a longitudinal axis of the bias member, or both. The guides may function to guide a post into contact with a bias member. The guides may function to allow a post to move between two contact surfaces. The guides may function to guide the posts longitudinally while contact surfaces on one or both sides of the guides contact the bias member so that the bias member is compressed. The guides may guide a post between two or more contact surfaces. The guides may be located proximate to the posts. For example, a rear guide may be located near a rear post and a forward guide may be located near a forward post. The forward guide may be located between the forward post and the hook latch. Preferably, the selection plate includes a forward guide and a rear guide. The forward guide may be part of a latch plate that is movable between a lockable state and an unlockable state. The guides may be axially moved with the latch plate so that when moved to a locking state the guides receive a post and a contact surface of the guide may be contacted by the bias member, and when the guide is moved to an unlocking state the guides may be free of contact with the bias member. The guides may be located along a sliding axis, a longitudinal axis of the bias member, a longitudinal axis of the handle, or a combination thereof. The guides may be "U" shaped, C shaped, have shoulders (i.e., contact surfaces) that extend from a recessed portion, or a combination thereof. The guides may be an absence of material that a post may extend through. The guide may be sufficiently small so that a bias member cannot extend through the guide. The guides may permit the posts to extend into a recess while an overhang of the bias member contacts a rear contact surface, a forward contact surface, or both of the guide on one or both sides of the recess. The guides may assist the latch plate in along the sliding axis, the longitudinal axis of the bias member, the longitudinal axis of the handle, or a combination thereof. The guides may have a recess that permits the posts to extend a predetermined distance and once the posts reach the end of the recess the posts may be prevented from traveling further. The guides or preferably the contact surfaces of the guides may further compress the bias member. For example, the spring may be pre-compressed (e.g., 1 N) and upon contact of the bias member with the guide the compression of the bias member may be increased (e.g., to 2 N). The guides may be free of travel when the selection plate is in the locked state or the unlocked state. A contact surface may be located on one or both sides of the guides and the bias device may contact the contact surfaces as the posts travel into the guide and the contact surfaces may restrict travel of the posts, the latch plate, or both while compressing the bias member.

The rear contact surface and the forward contact surface (hereinafter contact surfaces) may function to assist in compressing the spring as the latch plate, the selection plate, or both move. The contact surface may be a portion of a wall that a bias member contacts. The contact surfaces may be a shoulder located on each side of the guide. The contact surfaces may be a portion of the guide that a bias member contacts to compress a spring. The contact surfaces may be located proximate to the rear post, the forward post, or both so that as the post extends into a rear guide or the forward guide, the bias member contacts the rear contact surface or the forward contact surface respectively. The contact surfaces may be part of the selection plate, the latch plate, or both and the contact surfaces may impart all or a portion of a pre-load on a bias member. The contact surfaces may be static relative to the hook latch, the housing, the hand piece, the handle, or a combination thereof. The contact surfaces may move relative to the hook latch, independently of the hook latch, or both. The contact surfaces may have a taper. The contact surfaces may have a taper angle. The taper of the contact surface may be such that the contact surface gradually increases in distance from a bias member as the contact surface extends from a base to a top end. The base may be the end of the contact surface where a wall of the contact surface connects to a latch plate, a selection plate, or both. The angle of the taper may be about 10 degrees or less, preferably about 5 degrees or less, or about 3 degrees or less relative to a line or plane normal to a surface of the latch plate or the selection plate. The angle of the taper of the contact surface may be about 0.5 degrees or more, about 1 degree or more, or about 2 degrees or more relative to a line or plane normal to a surface of the latch plate or the selection plate. The rear post, the forward post, or both may have a length that is longer than a cross-sectional length of the bias member. The rear contact surface and the forward contact surface may be located a distance apart. The distance between the rear contact surface and the forward contact surface may be substantially equal to the distance between the forward post and the rearward post (e.g., within about 5 mm or less, about 3 mm or less, or about 1 mm or less). The taper of the contact surface may be opposite a taper of the posts so that a bias member contacts a base of the posts on a top and the bias member contacts a base of the contact surface on a bottom that is opposite the top (e.g., if the bias member has a circular cross cross-section the contact locations are 180 degrees apart). The contact surfaces may be part of the selection plate, the latch plate, or both and the location of the contact surfaces relative to the bias member, the posts, or both may be moved by moving the selection plate.

The selection plate may function to change the closure assembly between a lockable state and an unlockable state. The selection plate may move along a sliding axis to activate and deactivate the closure assembly (e.g., change the latch unit between a lockable state and an unlockable state). The selection plate may move so that the one or more posts the bias member, or both are moved from a contact state (e.g., lockable state) to a non-contact state (e.g., unlockable state) with the guides. The selection plate may allow a user to enable and disable the closure assembly. The selection plate may be substantially entirely located within the housing, hand piece, handle, or a combination thereof. The selection plate may include a rear post, a rear cross bar, a forward post, a forward cross bar a hook latch, a wall guide, one or more walls with one or more contact surfaces, a rear guide in a wall with a contact surface, a forward guide in a wall with a contact surface, or a combination thereof. The selection plate may include a forward guide, a rear guide, an adjustment switch, a contact surface, or a combination thereof. The selection plate may include an adjustment switch that extends out of the housing, hand piece, handle, or a combination thereof an is exposed for movement by the user.

The adjustment switch may function to move the closure assembly, deactivate the closure assembly, activate the closure assembly, or a combination thereof. The adjustment switch may be exposed so that upon a force being applied to the adjustment switch the state of the closure assembly is changed. The adjustment switch may be a thumb switch. The adjustment switch may include one or more gripping portions. The adjustment switch may contact the walls of the housing as the selection plate moves so that a longitudinal distance of movement of the selection plate is restricted. The adjustment switch may be movable along a switch path. The switch path may be parallel to the sliding axis. The switch path and the sliding axis may be coplanar. The adjustment switch may move the selection plate so that a detent pin is moved between the unlockable state detent and the lockable state detent to change the function of the closure assembly (e.g., activate and deactivate).

The unlockable state detent functions to allow free movement of the movable member and the ground member relative to each other by locking the position of the latch unit out of the path of the movement unit. For example, when the selection plate is moved to be locked at the unlockable state detent the triggers may freely move relative to the hand piece, the handle, the housing, or a combination thereof. The unlockable state detent functions to lock the latch plate, the hook latch, or both out of alignment with the bar, the closure assembly, or both so that a lockable state is not created. The lockable state detent functions to restrict movement of the movable member and the ground member relative to each other by locking the position of the latch unit, the latch plate, the hook latch, or a combination thereof in the path of the movement unit. The unlockable state detent and the lockable state detent (hereinafter detents) may lock the selection plate, the latch plate, or both in a lockable state or an unlockable state. The detents may allow a user to select if the closure assembly is activated. The detents may allow a user to longitudinally move the adjustment switch between positions and lock the adjustment switch is a desired state. The detents may be a recess that receives a pin or a pin that extends into a recess. The detents may prevent movement once a state is selected. The detents may be located on one or both sides of the selection state. Preferably, each side of the selection plate includes at least two detents. The detents may positively receive a pin. The detents may be sinusoidal in shape. The detents may have two or more valleys and each valley may be separated by a peak. Preferably, the detents include at least three peaks with a valley between the three peaks forming a lockable state detent and an unlockable state detent. Once the pin gets over the peak the pin may fall into a valley and lock. Each detent may be present to form a bi-stable latch plate. For example, the detent or latch plate either is locked or unlocked. The detents may assist in moving a pin into a locked state once the pin receives a predetermined point and if the pin does not reach the predetermined state then the pin returns to another detent until a stable state is obtained.

The detent pin functions to create a locked state, an unlocked state, or both with the closure assembly. The detent pin functions to contact a detent and then lock the selection plate in a selected location. The detent pin may be a projection that extends into and is received by the detent. The detent pin may flex as the detent pin moves from one detent to another detent. The detent pin may be static relative to the selection plate, the handle, housing, hand piece, or a combination thereof and the detents may flex during movement of the selection plate. The detent pin when located within a detent may restrict movement of the selection plate until a user acts upon an adjustment switch. The detent pin may be part of the housing, the handle, the hand piece, or a combination thereof. The detent pin may ground (e.g., prevent movement of) the closure assembly, the latch unit, the selection plate, or a combination thereof. The one or more detents may act as a stop; however, the closure assembly may include a rear stop, a forward stop, or both to constrain movement of the selection plate relative to the latch plate or vice versa.

The forward stop, the rear stop, or both (hereinafter stops) may function to prevent the selection plate and the latch plate from being moved out of axial alignment, the bias member from being over constrained, the bias member from being moved off of the rear post, rear crossbar, forward post, forward cross bar, or a combination thereof. The stops may be a back up to the detents to prevent movement of the selection plate beyond the detents. The stops may prevent a user from damaging the bias member. The stops may be a rear stop and a forward stop with the selection plate located there between. There may be two rear stops and two forward stops (e.g., one on each side (i.e., in the four corners)). Preferably, the stops are free of contact with the selection plate. The stops may be an emergency stop in an event of failure of a detent. The stops may be part of the latch plate or the housing so that the selection plate may remain constrained within a predetermined location relative to the latch plate, the housing, or both.

The one or more latch plates may function to move when a hook latch is contacted by a bar so that a locked state, an unlocked state, or both are created. The one or more latch plates may function to move when the hook latch is positioned in the prescribed path of the bar, along a forward stroke, a return stroke, or a combination thereof. The latch plate may carry one or more elements that form the pathway. The latch plate may carry the posts, the bias member, the hook latch, the wall guide, or a combination thereof. The latch plate may be generally static (relative to what? To the handpiece, to the ground member) and then movable (relative to what?) once acted upon by the movement unit. The latch plate may only move when the latch unit is in a lockable state (e.g., during locking or unlocking of the closure assembly or moving the closure assembly between a lockable state and an unlockable state). The latch plate may only move when contacted by the movement unit. The latch plate may move along the sliding axis, tracks, the hand piece, the housing, or a combination thereof. The latch plate may move along one or more tracks in or along the housing.

The tracks may function to guide the latch plate parallel to the sliding axis. The one or more tracks may function to movably connect the latch plate to the selection plate. The tracks function to assist the latch plate is moving along a predetermined path. The tracks assist the latch plate in moving along an axis. The tracks may be protrusions in the housing that extend into contact with the latch plate. The tracks may be one or more raised surfaces that the latch plate moves along. The tracks may be one or more raised surfaces that the selection plate move along. The one or more tracks may be integrally formed with the latch plate, the selection plate or both. A track may be on a first side, a second side, or both sides of a latch plate, a selection plate, or both. Preferably, the latch plate or the selection plate includes four tracks (e.g., two on each side). Preferably the tracks are two or more raised surfaces in the housing that the latch plate connects to or moves along. The tracks may be recesses in the housing that a portion of the latch plate extends into. The latch plate may move along the tracks when the latch unit is biased by the movement unit and as the latch plate moves the bias member may be compressed. The one or more tracks may prevent the latch plate and the selection plate from being separated as the latch plate and selection plate move relative to each other. The one or more tracks may move along rails or vice versa. The one or more tracks may prevent movement of the latch plate normal to the selection plate. The one or more tracks may extend cantilever from the selection plate, the latch plate, or both. The one or more tracks may extend outward and curve or bend. The one or more tracks may have an "L" shape. The one or more tracks may slide over the rails.

The one or more rails may function to connect the latch plate to the selection plate. The one or more rails may work in conjunction with the tracks. The one or more rails may guide the tracks during movement. The one or more rails when coupled to the tracks may prevent orthogonal movement or normal movement of the latch plate to the selection plate. The one or more rails may extend cantilever from the latch plate, the selection plate, or both. The one or more rails may be integrally formed with the latch plate, the selection plate or both. A rail may be on a first side, a second side, or both sides of a latch plate, a selection plate, or both. Preferably, the latch plate or the selection plate includes four rails (e.g., two on each side). The rails may allow for longitudinal movement and prevent movement in a direction other than the longitudinal movement. The rails may be an integral part of the latch plate, the selection plate or both. The latch plate may include one or more rails and one or more tracks. The selection plate may include one or more rails and one or more tracks. The rails may be located on a bottom, a first side, a second side, or a combination thereof of the selection plate, the latch plate, or both. The one or more rails and tracks may assist in pre-loading the bias member, loading the bias member, or both.

The bias member may function to store energy when a force is applied to the latch plate and then to the energy when the force is removed. The bias member may function to move the latch plate back towards home position. The bias member may assist in locking or unlocking the movable member and the ground member. The bias member may be any material that may store energy. The bias member may be elastomeric, rubber, a spring steel, helical, round, cylindrical, or a combination thereof. The bias member may be a piece of rubber that is compressible. Preferably, the bias member is a compression spring that stores and releases energy. The bias member when located within the latch unit and the latch unit being in a home position may have a pre-load. The pre-load may be greater than 0 N, about 0.2 N or more, about 0.5 N or more, about 0.75 N. or more, or about 1 N or more. The pre-load may be about 30 N, or less about 20 N or less, or about 10 N or less. Preferably, the preload is about 0.5 N or more and more preferably about 0.066 N or more. A load on the bias member may be increased when the latch unit moves in a first direction, a second direction, or both relative to a home position of the latch unit. An increase in load or a change in load may be about 1 N or more, about 3 N or more, about 5 N or more, about 7 N or more, or about 10 N or more. The increase in load or the change in load may be about 50 N or less, about 30 N or less, about 20 N or less, or about 15 N or less. The change in load on the bias member may exponentially increases as a distance of the latch unit form a home position increases. The change in load may be sufficiently large so that the bias member returns the latch unit back to the home position when the latch unit moves from a locked state to an unlocked state, in an unlockable state, a lockable state when the hook latch is not biased, or a combination thereof. The bias member may be a double acting bias member. The bias member may bias towards the home position regardless of whether the bias member is biased in a first direction or a second direction. The bias member may be compressed when the hook latch is contacted by the bar.

The hook latch may function to create the locked state. The hook latch may function to catch the bar and prevent movement of the movable member relative to the ground member. The hook latch may have two sides or more, three sides or more, or four sides or more. The hook latch may have a first side (e.g., an entry portion) that assists in creating a locked state. The hook latch may have a second side (e.g, a return portion) that assist in retaining a bar so that the locked state is maintained. The hook latch may have a third side that assists in creating an unlocked state. The hook latch may be generally triangular in shape or may have a portion that is triangular in shape. The hook latch when contacted may longitudinally move the latch plate. The hook latch may include an angled portion, a linear portion, an entry apex, entry portion, exit portion, exit apex, pocket, or a combination thereof.

The one or more entry portions may function to assist in creating a locked state when the bar contacts the entry portions. All or a portion of the one or more entry portions extend across the latching pathway when the selection plate is in the lockable state. The one or more entry portions may be removed from extending across the latching pathway when the selection plate is in the unlockable state. The one or more entry portions may be angled so that all or a portion of the one or more entry portion extends across an opening of the latching pathway so that as the movable member moves along the prescribed path in the forward path the bar moves through the latching pathway into contact with the entry portion. The one or more entry portions may extend in the path of the prescribed motion of the bar so that the bar contacts the entry portion. The entry portion may be angled so that as the bar traverses along the prescribed motion the bar is moved towards the entry apex and ultimately the pocket. The entry portion may be linear (e.g., a linear portion) or angled (e.g., an angled portion). The entry portion may have a sufficiently small angle so that as the bar moves along the entry portion the latch plate is moved, biasing the bias member, by a force being exerted upon the entry portion of the hook latch. The latch plate may continue to move as the bar travels along the entry portion until the bar reaches the entry apex. The entry portion may terminate at an entry apex.

The entry apex may function to assist the bar in entering the pocket. The entry apex may prevent the bar from exiting the pocket from a same direction the bar entered the pocket. The entry apex may be where two walls converge together. The entry apex may be a point where a bar may be required to be on a first side or a second side. The entry apex may create a lip at the pocket so that the bar cannot be back driven. When the bar passes the entry apex the bias member may release its stored energy so that the bar is moved into the pocket. The entry apex and an exit apex may be located on opposing sides of the pocket.

The pocket may function to receive the bar so that a locked state is formed. The pocket may be a wall that the bar is biased against so that the bar is restricted from being moved back into the latching pathway. The pocket may be a recess that the bar resides within so that the locked state is formed and the bar is not inadvertently moved out of the pocket. The pocket may resist a biasing force of the movable member away from the ground member. The pocket may prevent longitudinal movement of the bar. The exit apex, the entry apex, or both may extend beyond the pocket so that the bar remains within the pocket until a bias force of the movable member is resisted, a user regrips the movable member and the ground member together, or both. Upon regripping, resisting a bias force or both the bar may exit the pocket by extending around the exit apex.

The exit apex may function to prevent a bar from inadvertently exiting the pocket. The exit apex may extend beyond the pocket. The exit apex may be a point that once the bar extends beyond the bar cannot reenter the pocket. The bar may contact the exit apex while exiting so that the latch plate is biased, and upon the bar stopping contact with the exit apex, the latch plate may bias away from the bar so that the prescribed motion of the bar is above the pocket and the bar cannot reenter the pocket. The exit apex may be formed between the pocket and the return portion.

The return portion may function to guide the bar from the locked state to an unlocked state. The return portion may function to guide the bar to the latching pathway. The return portion may be located below the prescribed path when the latch plate is in the return position. The return portion may be located above the latch plate when the latch plate is in the home position. For example, the hook latch may block the latching pathway when the latch plate is in the home position, and as the bar moves along a prescribed path the bar may contact the return portion of the hook latch and move the hook latch to open the latching pathway. As the latching pathway is being opened the bias device may be compresses an energy stored within the bias device. Once the bar stops contacting the return portion (e.g., leaves the pathway) and reenters the latching pathway the bias device may bias the latch plate back to a home position.

The pathway may function to guide the bar from a home position to a locked position, from a locked position to an unlocked position, from an unlocked position to a home position, or a combination thereof. The pathway may assist a bar in circumnavigating a hook latch. The pathway may be tortuous. The pathway may be a labyrinth. The pathway may be an open area in the movement unit that the bar is guided through. The pathway may be an area between two or more walls that a bar moves through, a bar moves along, or both. The pathway may be linear. The pathway may have curved portions, arcuate portions, straight portions, extend 360 degrees, have serpentine portions, or a combination thereof. The pathway may begin and end at a latching pathway. The pathway may extend along an entry portion, along a return portion, around an entry apex, into a pocket, around an exit apex, into a wall guide, around a guide apex, around a release apex, along a rear wall, or a combination thereof. The pathway may assist the bar in moving along one or more walls of the hook latch. The pathway may assist the bar in moving the latch plate as the bar and the hook latch contact each other. The pathway may be out of contact with the hook latch, the wall guide, or both when the latch unit is in the unlocked position, the unlocked state, or both. The pathway may extend between the hook latch and the wall guide. The pathway may permit the bar to move around the release apex of the hook latch, move into contact with the wall guide, or both.

The release apex may function to guide the bar into the pathway and out of the pathway. The release apex may align an entry end of the pathway with the latching pathway when the latch unit is in the locked state. The release apex may align an exit end of the pathway with the latching pathway when the latch unit is in the locked state. The release apex may move from a first side of a latching pathway to a second side of a latching pathway. The release apex may connect the pathway to the latching pathway. The release apex may form a point of the hook latch. The release apex may be a beginning and end of the hook latch. The release apex may be located opposite the pocket. The release apex may be located opposite the wall guide.

The one or more wall guides may function to assist the bar in moving from a locked position to an unlocked position, an unlocked position to a locked position, or both. The one or more wall guides may restrict movement in a first direction (e.g., vertically, towards a forward post), in a vertical direction, or both when the bar is moving from an unlocked position to a locked position. The one or more wall guides may assist a bar in extending around an exit apex. The one or more wall guides may extend into the pathway to restrict movement of the bar. The one or more wall guides may include a guide apex and a rear wall. The one or more wall guides may include a guide apex that extends into the pocket, towards the hook latch, or both.

The one or more guide apexes may function to prevent the bar from moving through the pocket without a locking state being formed, without the bar being in the locked position, or both. The one or more guide apexes may divide a pocket in half. The guide apex may be located between the entry apex and the exit apex. The guide apex may be substantially linear, angled downward, angled toward the entry apex, or both. The guide apex may overlap the exit apex. For example, a mid-point extending between the hook latch and the wall guide may be crossed by both the hook latch and the wall guide. The guide apex may interfere in the pathway so that as the bar moves around the entry apex the bar may contact the guide apex so that when a trigger, a movable member, or both are released the bar moves the pocket. The guide apex may not contact the bar but may guide the bar into contact with the exit apex so that the bar is retained within the pocket and a locked state is created. The guide apex may be located under a rear wall. The guide apex may connect to the wall and the rear wall may connect the guide apex to the wall.

The rear wall may function to guide the bar around the exit apex. The rear wall may extend at an angle relative to the guide apex. The rear wall may angle away from the exit apex towards a wall. The rear wall may extend away from the exit apex. The rear wall may extend from a location below the exit apex to a location above the exit apex. The rear wall may guide the bar around the exit apex as a user applies a force to the trigger, the movable member, or both so that the bar moves away from the pocket towards the rear wall. The rear wall may guide the bar as the bar moves along a prescribed motion, an arcuate movement, or both.

The arcuate movement may function to move the bar from a home position, to a locked position, to an unlocked position, or a combination thereof. The arcuate movement may be a movement of the bar, the trigger, a movable member, or a combination thereof as the bar, the trigger, a movable member, or a combination thereof rotate about a pivot. The arcuate movement may be a prescribed movement of the bar, the trigger, the movable member, or a combination thereof. The arcuate movement may be the only movement the trigger, the bar, the movable member, or a combination thereof makes. The arcuate movement may move the bar from a home position to a locking position, a locking position to an unlocked position, and an unlocked position back to a home position.

The home position may be a position of the bar when the bar is not located within the handle, the latch unit, the housing, the hand piece, or a combination thereof. The home position may be a position where the latch plate is at steady state, the bar is not within the latch unit, or both. The home position may be a position where the bias member is pre-compressed but the latch unit is not being biased. The latch plate may move from a locked position to a home position or vice versa, an unlocked position to a home position or vice versa, or both. The home position may be where the hook latch crosses the latching pathway. The home position may be where the bias member returns the latch plate upon an engagement force or a disengagement force being removed. The home position may be where the movement unit and the latch unit are disconnected, can move relative to each other, or both. The bar may move from an unlocked position to a home position. The bar may move from a locking position to an unlocking position and then to a home position.

The locking position may be where the bar is located within the pocket and the bar is prevented from moving by the hook latch. The locking position may be where the bar is located between the entry apex and the exit apex. The locking position may be where the movable member moves the bar back towards the hook latch so that the bar is retained in the pocket and the movable member is prevented from moving. The locking position may be the position where the bar prevents the movable member, a trigger, or both from moving. The locking position may be where the hook latch is aligned with the latching pathway. In the locking position, the hook latch may be pre-biased. In the locking position, the bar may bias the hook latch up or in a first direction (i.e., towards a forward post) as the bar enters the pathway. In the locking position, the bar may bias the hook latch down or in a second direction, which is opposite the first direction (i.e., towards a rear post) as the bar exits the pathway. In the locking position, the hook latch may be moved by the bar as the bar moved along the arcuate movement, the pathway, or both. The latch plate may be locked in the locking state detent when the latch unit is in the locking position. The locking position may be located between two unlocked positions.

The unlocked position may function to allow the bar to move within the pathway. The unlocked position may function to move the hook latch, latch plate, or both out of alignment with the bar, the latching pathway, or both. The unlocked position may be any position where the bar is within the pathway but not located within the pocket. The unlocked position may be a bar in the pathway moving along the entry portion, the return portion, or both. The unlocked position may be where the bar is not located between the entry apex and the exit apex. The unlocked position may be where the latch plate, hook latch, or both are locked out of the prescribed motion, the arcuate movement, or both of the movement unit, the bar, or both. In the unlocked position, the hook latch may lock the bar out of the arcuate movement or the hook latch may be moved out of alignment with the bar so that the bar is free to move in and out of the latch unit within creating a locked state. For example, a trigger connected to the bar may be free to move about a pivot. In the unlocked position, the hook latch may be locked out of alignment with the latching pathway, the arcuate movement, the prescribed motion, or a combination thereof of the bar. In the unlocked position, the latch plate may be in the unlocking state detent. The bar may make a locking movement so that the bar changes from an unlocked position to a locked position.

The locking movement may be where the bar extends from an unlocked position to a locked position. The locking movement may be where the bar extends around an entry apex. The locking movement may be where the bar moves into contact with the guide apex and then upon release of the trigger, the movable member, or both the bar is moved into the pocket, from the guide apex into the pocket, into contact with the exit apex but retained in the pocket, or a combination thereof. The locking movement may be where the bar enters the pocket. The locking movement may be followed by an unlocking movement where the bar is released from the pocket.

The unlocking movement may function to release the bar from the pocket. The unlocking movement may be a movement around the exit apex. The unlocking movement may be a movement from the pocket to the wall guide where the wall guide assists in moving the bar around the exit apex, to a location above the exit apex, or both. The unlocking movement may extend away from the hook latch and then back towards the hook latch once the bar is above the exit apex. The unlocking movement may result in the bar being un an unlocked state. An unlocking may move the selection plate between a lockable state and an unlockable state.

The unlockable state may function to prevent the closure assembly to be locked. The unlockable state may be a state where the latch unit is configured to be out of a movement path of the movement unit so that a locked state cannot be formed. The unlockable state may be where the latch state is moved to a second position where the latch unit and the movement unit are not aligned. The unlockable state may be where the hook latch is mis-aligned with the latching pathway so that as a bar extends into the latching pathway the bar and hook latch do not contact each other. In the unlockable state, the hook latch may be located entirely above or below the latching pathway. The unlockable state may be a state where the detent pin is located within the unlockable state detent. When the selection plate is moved from the unlockable state detent to the lockable state detent the closure assembly may change from the unlockable state to the lockable state.

The lockable state may function to allow the closure assembly to be latched. The lockable state may be a state where the movement unit and the latch unit are aligned and may connect together, may lock a movable member to a ground member, or both. The lockable state may be where a portion of the hook latch is aligned with the latching pathway so that as a bar extends through the latching pathway the bar can contact the hook latch to create a locked state. In the lockable state, the bar may contact the hook latch and move the movement unit. The closure assembly, in the lockable state may have an unlocked state or a locked state. The unlocked state may be where the movable member and the ground member are movable relative to each other. The unlocked state may be where the bar is not constrained by the latch unit. The unlocked state may be where the latch unit is not locked relative to the movement unit and the latch unit and the movement unit may move relative to each other. The unlocked state may be where the latch plate is locked so that the bar extends into the pathway and is not constrained any members of the latch plate, the hook latch, or both. The unlocked state may allow a user to freely open and close the jaws without the jaws being locked in place. The latch plate, in the unlocked state, may be locked in a position so that the movable member and the ground member are unlocked. The unlocked state may be where the latch unit is in a lockable state but the bar is not located within the pocket so that the bar is movable relative to the hook latch. The bar in the unlocked state may be in contact with any part of the hook latch except for the pocket. The latch unit may in a lockable state and changed between a locking state and an unlocking state, the bar may be movable between a locking state and an unlocking state, or both.

The locking state may function to lock the movable member and the ground member together. The locking state may be where the closure assembly is locked. The locking state may be where the movement unit and the latch unit are connected together. The locking state may be where the latch unit is moved along the sliding axis and restrained by the bar. The locking state may be where the latch unit, the hook latch, or both are movable by the movement unit to lock the movable member and the ground member together. The locking state may be where the latch plate is restricted from moving about a sliding axis by the bar.

The sliding axis may function to move the latch plate from a first position to a second position, along the track, up and down, parallel to a length of the handle, or a combination thereof. As the latch plate moves along the sliding axis compression of the bias member may be increased, decreased, or a combination of both. The as the bar moves along the hook latch, an engaging force may be applied to the hook latch that moves the latch plate along the sliding axis.

The engaging force may function to move the latch plate along the sliding axis, to compress the bias member, to lock the closure assembly, to lock the movement unit to the latch unit, or a combination thereof. The engaging force may be sufficiently large to move the latch plate as the bias member compresses. The engaging force may increase as the bar moves along the hook latch. The engaging force may increase as the bar moves from the release apex towards the entry apex. The engaging force may increase as the bar moves along the return portion. The engaging force may increase as the bar moves from the exit apex to the release apex. Preferably, the engaging force is along a first side of the hook latch, along the entry portion, or both as the bar extends from the latching pathway and the pathway and into the pocket. The engaging force may be a single force that is generated by a user as the bar moves along a prescribed movement an arcuate movement, or both. The user may generate the engaging force by moving the movable member and the ground member towards each other. The engaging force may be substantially similar to an amount of force required for a disengaging force.

The disengaging force may function to move the bar out of the pocket, around the exit apex, or both. The disengaging force may extend parallel to the engaging force. The disengaging force may have one or more forces along one or more different directions, vectors, or both. The disengaging force may remove a bar from the pocket and then remove the bar from the latch unit, the housing, the handle, the hand piece, or a combination thereof. The disengaging force may have a portion that is along the exit apex, along the wall guide, along the return portion, or a combination thereof. The disengaging force may be created by a regripping and movement of the movable member relative to the ground member. The disengaging force may first extend away from the hook latch, then up the rear wall, around the exit apex, and then along the return portion where the latch plate is moved along the sliding axis. The disengaging force may have a first disengaging force where the bar is moved out of the pocket and a second disengaging force where the bar is aligned with the latching pathway. The first disengaging force may move the bar away from the pocket (i.e., a regrip of the movable member or the trigger), up over the exit apex, or both. The first disengaging force may guide the bar along a rear wall of the wall guide. The first disengaging force may release the closure assembly, move the closure assembly from a locked state to an unlocked state, or both. Once the bar, movement unit, or both are released the bar, movement unit, or both may change from a first disengagement force to a second disengagement force. The second disengagement force may move the latch plate along the sliding axis so that the bar is aligned with the latching pathway. The second disengagement force may be sufficiently large to compress the bias member. The second disengagement force may increase as the bar moves along the prescribed motion, the arcuate movement or both. The second disengagement force may move the latch plate from a home position to an unlocked position where the bar may separate from the latch unit.

FIG. 1 is a rear perspective view of an electrosurgical device 2 including a handpiece 4 connected to forceps 10 by a stylet 6. The forceps 10 include a first working arm 20 with a first jaw 21 and a second working arm 22 with a second jaw 23. The handpiece 4 includes a housing 8 that encloses a portion of a closure assembly 32 that prevents movement of the first working arm 20 and the second working arm 22 by locking the movable member 12 and the ground member 14 in a position. The movable member 12 is a trigger 24 and the ground member 14 is a handle 26.

Figure 2A:
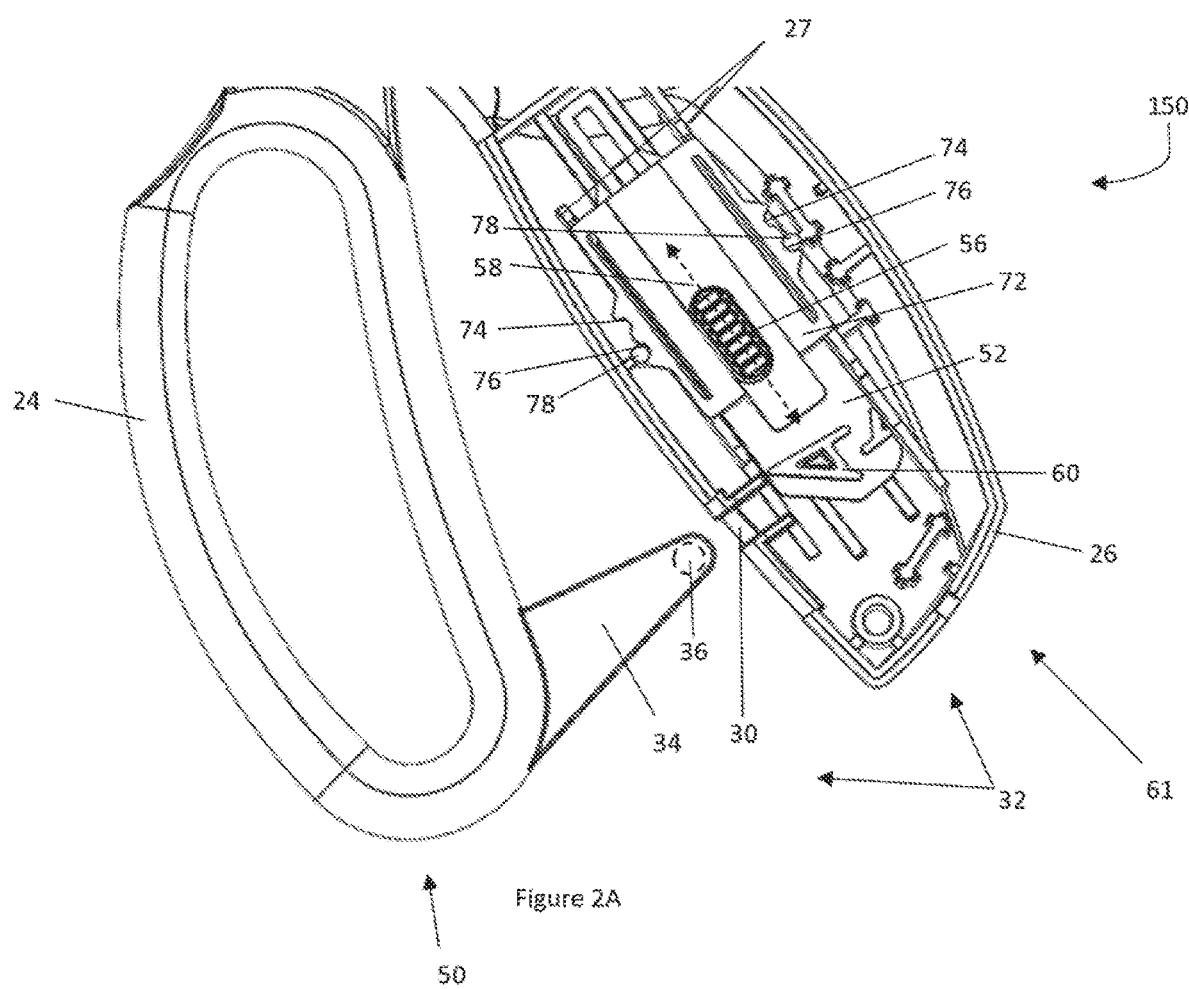
FIG. 2A is a close-up view of a movement unit and a latch unit in a lockable state.

FIG. 2A illustrates a laterally bisected, perspective view of a closure assembly 32 having a movement unit 50 and a latch unit 61. The closure assembly 32 shows the trigger 24 and a selection plate 72 in a locking state 150. The trigger 24 includes a bar arm 34 to which a bar 36 is attached. The bar 36 is configured to pass through a latching pathway 30 in the handle 26. In the locking state 150, the bar 36 is aligned with and configured to contact a hook latch 60, which is fixed to a latch plate 52. The latch unit 61 includes a selection plate 72, an adjustment switch 56, an unlocked state detent 74, a locking state detent 76, and a bias member (not shown). The adjustment switch 56 is fixed to the selection plate 72. The unlocked state detent 74 and the locking state detent 76 are formed in the selection plate 72. The unlocked state detent 74 and the locking state detent 76 are configured to accept a detent pin 78, which is affixed to the handle 26 and assist in restraining movement of the selection plate 72. The locking state 150 is enabled by moving the locking state detent 78 to accept the detent pin 78. The selection plate 72 is selectively movable with the adjustment switch 56 so that either the unlocked state detent 74 or the locking state detent 76 accept the detent pin 78. As will be seen below, the selection plate 72 is in mechanical communication with the latch plate 52. Thus, a movement of the adjustment switch 56 along a switch path 58 is mirrored by the hook latch 60. The handle 26 further includes rear stops 27 that prevent movement of the selection plate 27 beyond the locking state detent 76 in the event that the locking state detent 76 fails to restrain the selection plate 72.

Figure 2B:
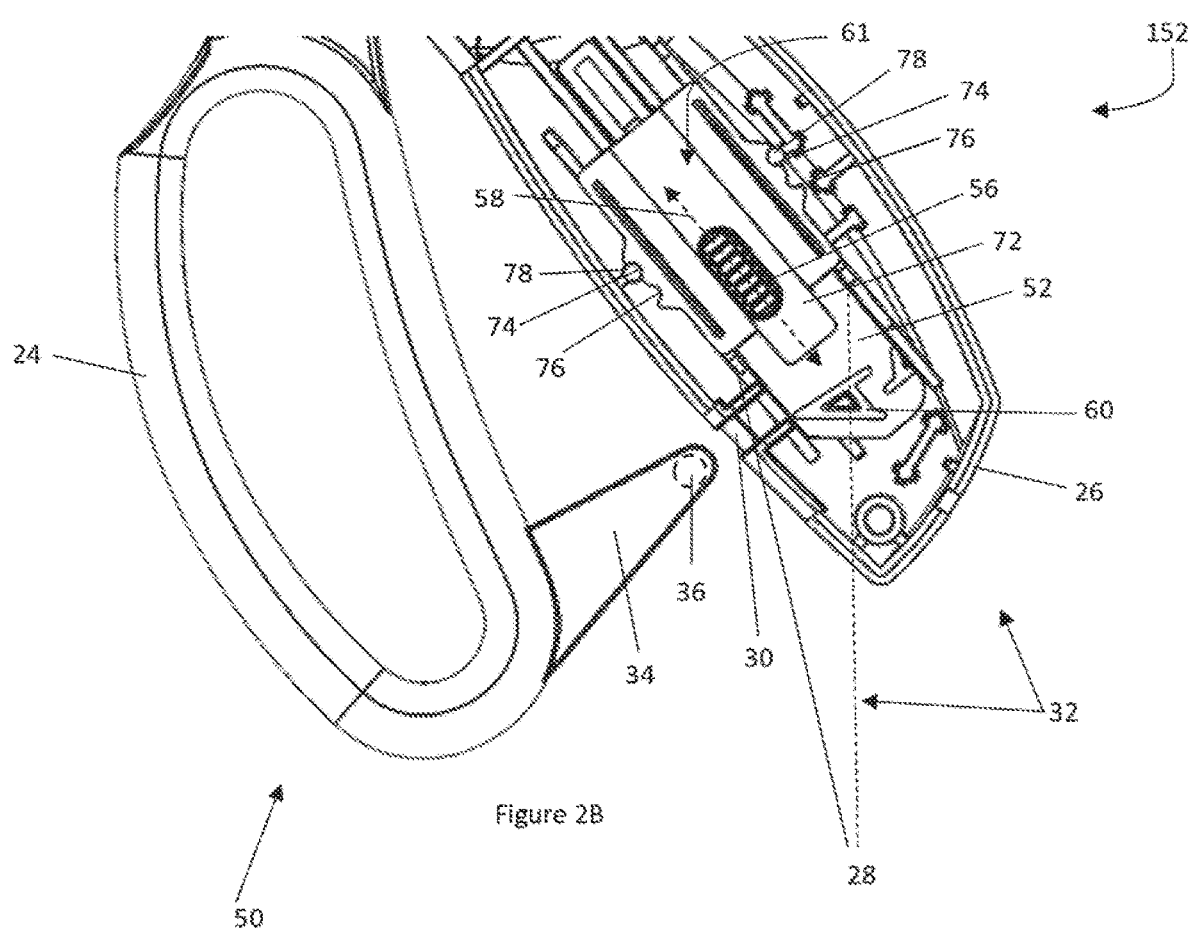
FIG. 2B is a close-up view of a movement unit and a latch unit in an unlockable state.

FIG. 2B illustrates a laterally bisected, perspective view of a closure assembly 32 including a movement unit 50 and a latch unit 61. The movement unit 50 includes a trigger 24 with a bar arm 34 and a bar 36 extending from the trigger 24, and the latch unit 61 having a selection plate 72 in an unlocked state 152. The bar 36 is configured to pass through the latching pathway 30 in the handle 2. In the unlocked state 152, the bar 36 is configured to pass by the hook latch 60, which is fixed to the latch plate 52, and be free of contact with the hook latch 60. The latch unit 61 includes the selection plate 72, the adjustment switch 56, the unlocked state detent 74, the locking state detent 76, and the bias member (not shown). The adjustment switch 56 is fixed to the selection plate 72, the unlocked state detent 74, and the locking state detent 76 are formed in the selection plate 72. The unlocked state detent 74 and the locking state detent 76 are configured to accept the detent pin 78, which is affixed to the handle 26. The handle 26 further includes forward stops 28 that restrict movement of the selection plate 72 in the event that the unlocked state detents 74 fail to hold the selection plate 72 in place. The unlocked state 152 is enabled by moving the unlocked state detent 74 to accept the detent pin 78. The selection plate 72 is selectively movable with the adjustment switch 56 so that either the unlocked state detent 74 or the locking state detent 76 accept the detent pin 78. As will be seen below, the selection plate 72 is in mechanical communication with the latch plate 52. Thus, a movement of the adjustment switch 56 along the switch path 58 is mirrored by the hook latch 60.

Figure 3A:
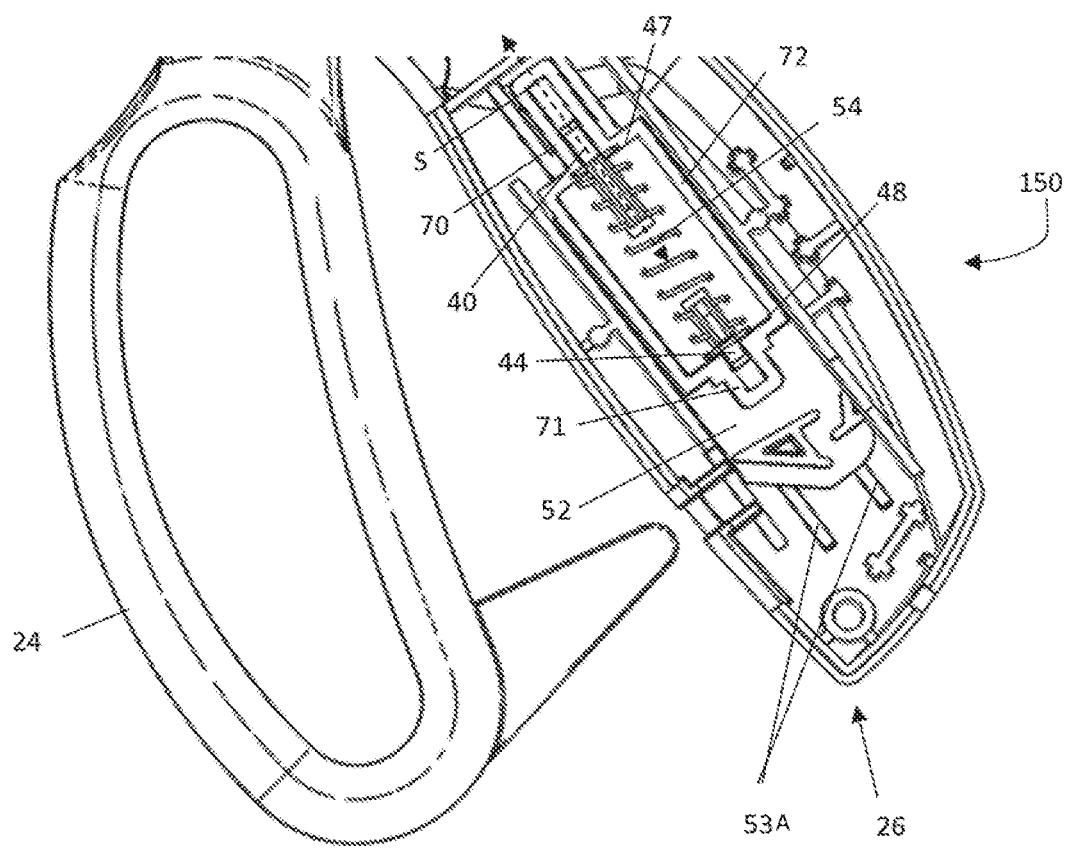
FIG. 3A is a close-up view of a movement unit and a latch unit in a lockable state with a portion the selection plate removed from the latch unit.

FIG. 3A illustrates a laterally bisected, perspective view of the handle 26 including the trigger 24 and a laterally bisected view of the selection plate 72 in the locking state 150. The selection plate 72 includes a rear contact surface 47, a forward contact surface 48, a rear guide 70, and a forward guide 71. The latch plate 52 may move along tracks 53A while the selection plate 72 is fixed. The latch plate 52 includes a rear post 40 and a forward post 44. In the locking state 150, manipulation of the latch plate 52 along a sliding axis S, in the direction of the rear contact surface 47, while the selection plate 72 is fixed, results in the bias member 54 compressing and exerting a load against the rear contact surface 47 while the rear post 40 travels to a greater depth within the rear guide 70. Conversely, the load of the bias member 54 on the forward contact surface 48 decreases as the bias member 54 is decompressed as the depth of the forward post 44 within the forward guide 71 decreases.

Figure 3B:
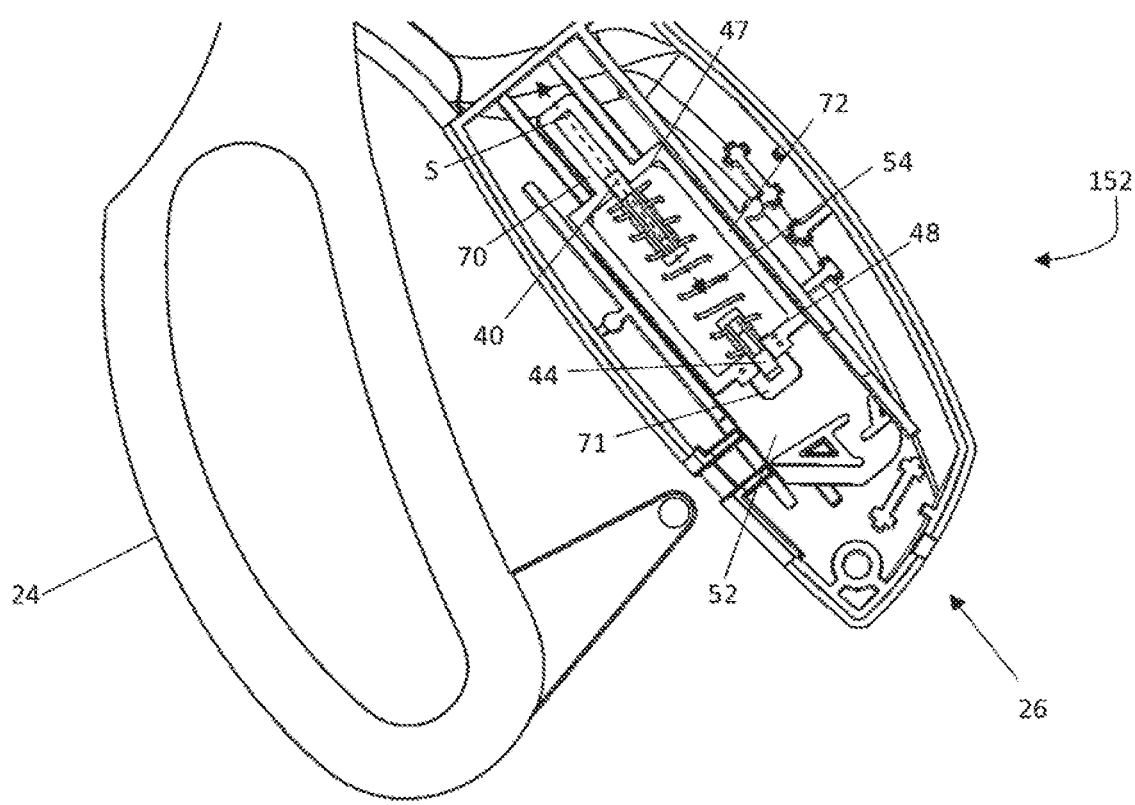

FIG. 3B illustrates a laterally bisected, perspective view of the handle 26 including the trigger 24 and a laterally bisected view of the selection plate 72 in the unlocked state 152. The selection plate 72 includes the rear contact surface 47, the forward contact surface 48, the rear guide 70, and the forward guide 71. The latch plate 52 may move while the selection plate 72 is fixed. The latch plate 52 includes the rear post 40 and the forward post 44. In the unlocked state 152, manipulation of the latch plate 52 along the sliding axis S, slides the latch plate 52 in the direction of the forward contact surface 48, while the selection plate 72 is fixed which results in the bias member 54 exerting a load against the forward contact surface 48 while the forward post 44 travels to a greater depth within the forward guide 71 so that the bias member 54 is loaded. Conversely, the load of the bias member 54 on the rear contact surface 47 decreases as the depth of the rear post 40 within the rear guide 70 decreases.

Figure 4:
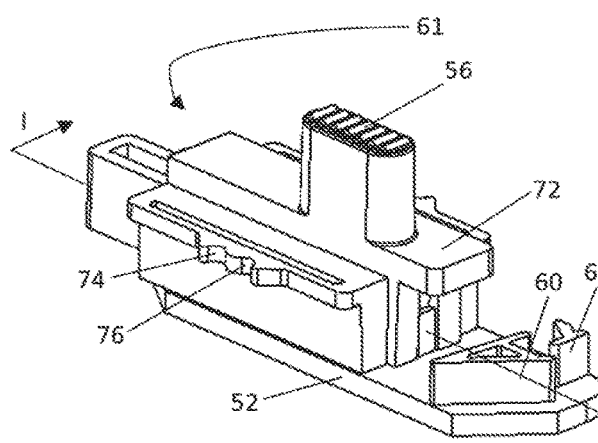
FIG. 4 is a perspective view of a latch unit.

FIG. 4 illustrates a perspective view of the latch unit 61 and the latch plate 52. The latch unit 61 includes the selection plate 72, the adjustment switch 56, the unlocked state detent 74, the locking state detent 76, and the bias member (not shown). The selection plate 72 is fixed atop the latch plate 52, which includes a hook latch 60 and a wall guide 65.

Figure 5:
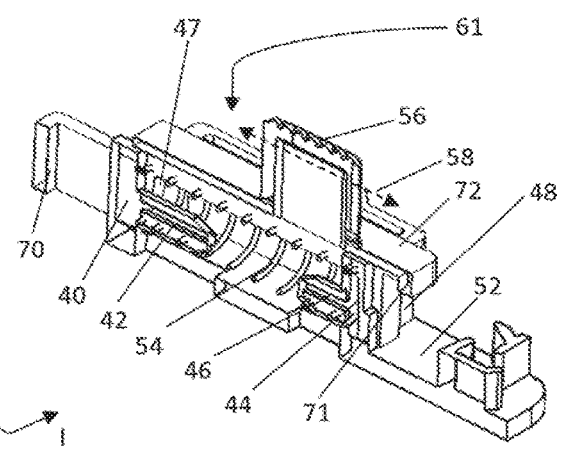
FIG. 5 is a cross-sectional view of the latch unit of FIG. 5 cut along lines I-I.

FIG. 5 illustrates a cross-sectional view of the latch unit 61 and the latch plate 52 along line I-I of FIG. 4. The latch plate 52 includes the rear post 40, a rear crossbar 42, the forward post 44, and a forward crossbar 46. The latch unit 61 includes the selection plate 72 and the bias member 54 which acts upon the selection plate 72 at the rear contact surface 47 and the forward contact surface 48. The bias member 54 contacts the latch plate 52 at the rear post 40 and the forward post 44. The bias member 54 is configured to reciprocally transfer movement of the selection plate 72 along the switch path 58 to the latch plate 52. The selection plate 72 is movable along the switch path 58 by actuating the adjustment switch 56. The selection plate 72 includes a forward guide 71 and a forward post 44 that are movable relative to each other and a rear guide 71 and a rear post 40 that are movable relative to each other.

Figure 6:
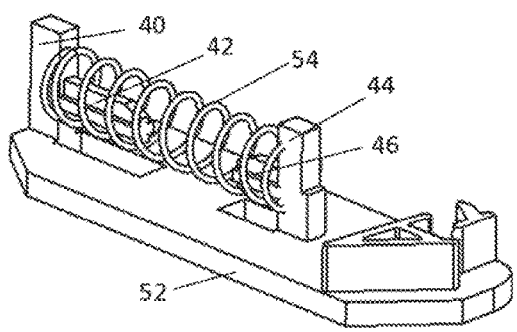
FIG. 6 is a perspective view of the latch unit with the selection plate removed.

FIG. 6 illustrates a perspective view of the latch plate 52 and the bias member 54. It can be seen that the rear post 40 and forward post 44 confine the bias member from extension and keeps the bias member 54 at a predetermined load. Further, the rear crossbar 42 and the forward crossbar 46 prevent the bias member 44 from being displaced from the rear post 40 and the forward post 44.

Figure 7:
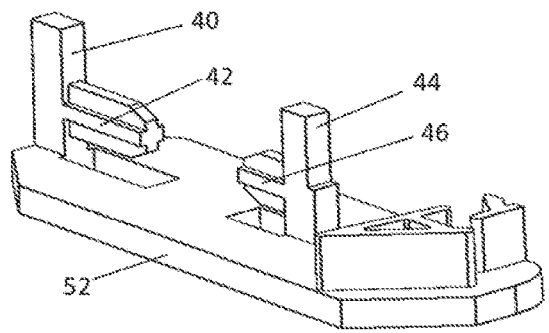
FIG. 7 is a perspective view of the latch plate with the selection plate and the bias member removed.

FIG. 7 illustrates a perspective view of the latch plate 52. The latch plate 52 includes the rear post 40 the forward post 44, the rear crossbar 42 and the forward crossbar 46.

Figure 8A:
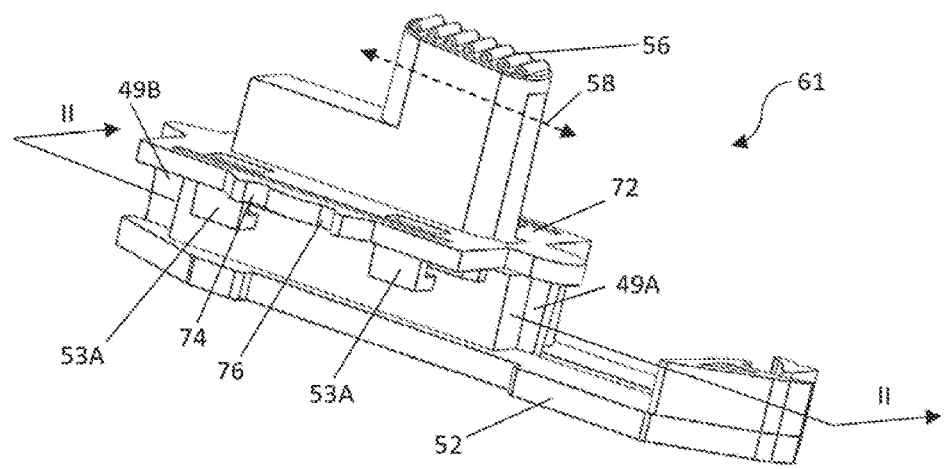
FIG. 8A is a perspective view of the latch unit.

FIG. 8A shows the latch unit 61 including the latch plate 52 and the selection plate 72. The selection plate 72 includes the adjustment switch 56, a track 53A, a forward movable bias constraint 49A, a rearward movable bias constraint 49B, the unlockable state detent 74, and the lockable state detent 76. The selection plate 72 fits on the latch plate 52. The selection plate 72 is movable along the switch path 58.

Figure 8B:
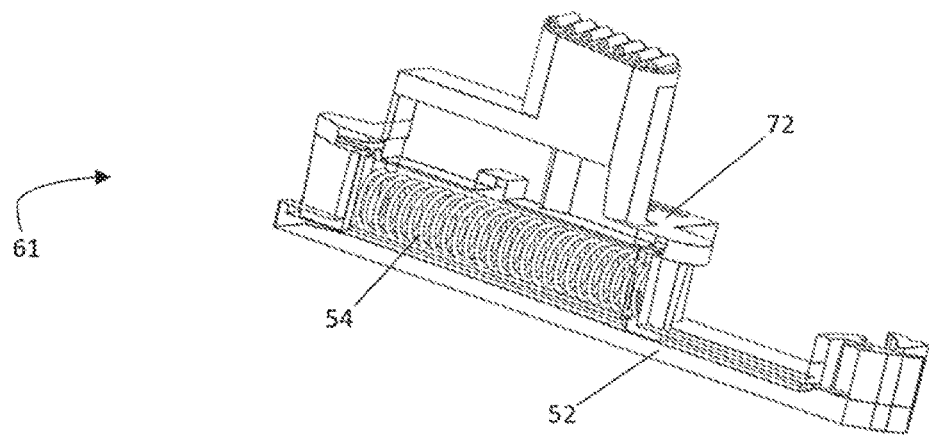
FIG. 8B is a cross-sectional view of the latch unit cut along line II-II.

FIG. 8B shows the latch unit 61 including the latch plate 52 and the selection plate 72 bisected along line II-II of FIG. 8A. The bias member 54 fits within the latch plate 52.

Figure 8C:
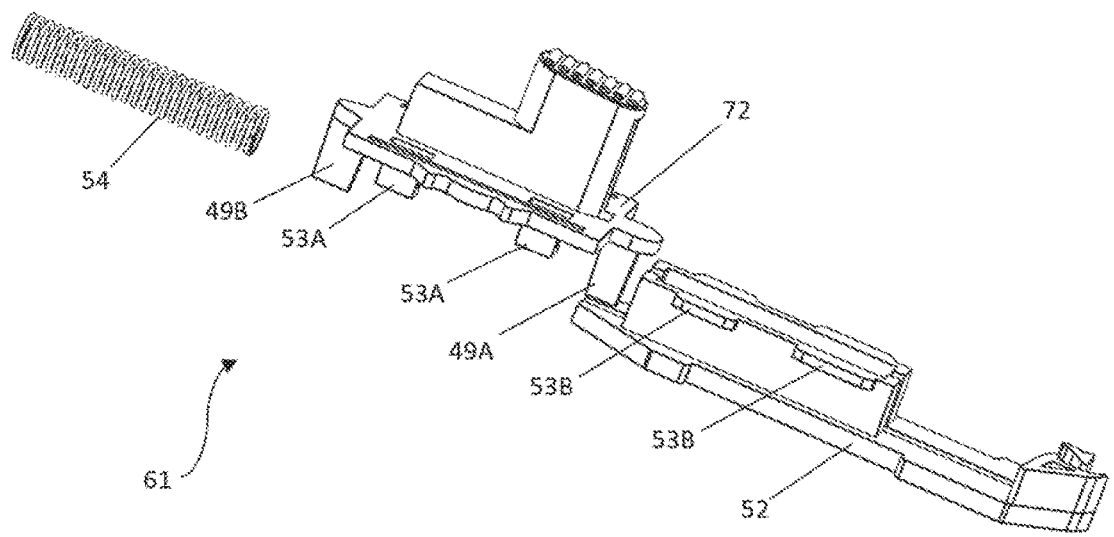
FIG. 8C is an exploded view of the latch unit.

FIG. 8C illustrates an exploded view of the latch unit 61 including the latch plate 52, the selection plate 72, and the bias member 54. The selection plate 72 includes the forward movable bias constraint 49A, the rearward movable bias constraint 49B, and the track 53A. The latch plate 52 includes a rail 53B. The track 53A aligns with the rail 53B allowing for free movement of the rail 53B within the track 53A.

Figure 8D:
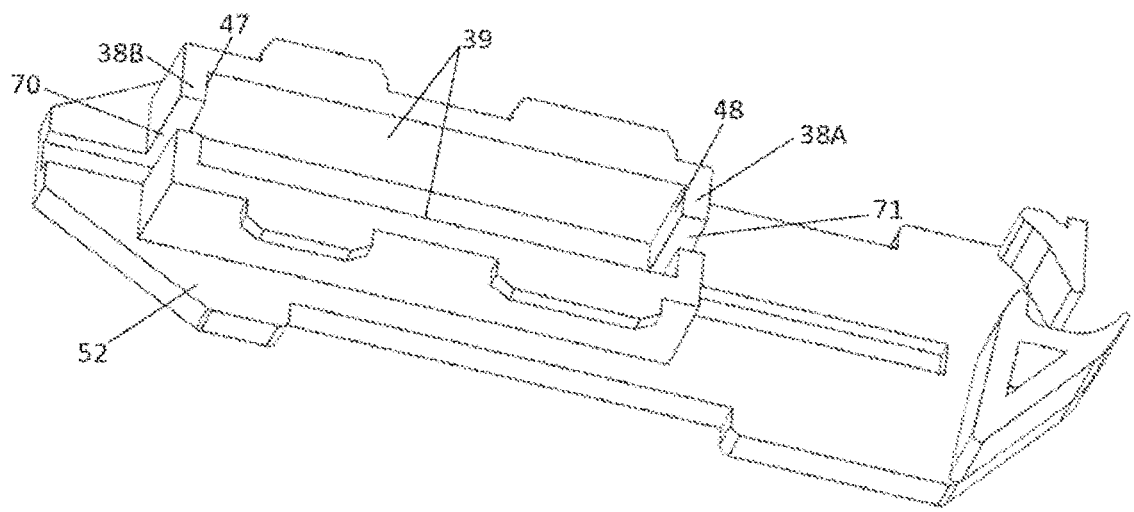
FIG. 8D is a perspective view of the latch plate.

FIG. 8D shows the latch plate 52 including a side constraint 39, a forward bias constraint 38A, a rearward bias constraint 38B, which form a boundary for the bias member (not shown). The forward bias constraint 38A includes the forward surface 48. The rearward bias constraint 38B includes the rear surface 47. A gap in the forward bias constraint 38A forms a forward guide 71. A gap in the rearward bias constraint 38B forms a rear guide 70. The rearward movable bias constraint (not shown) moves freely within the rear guide 70. The forward movable bias constraint (not shown) moves freely within the forward guide 71. The rear surface 47 and the forward surface 48 function to prevent axial elongation of the bias member (not shown). The side constraint 39 prevent bowing of the bias member (not shown).

Figure 9A:
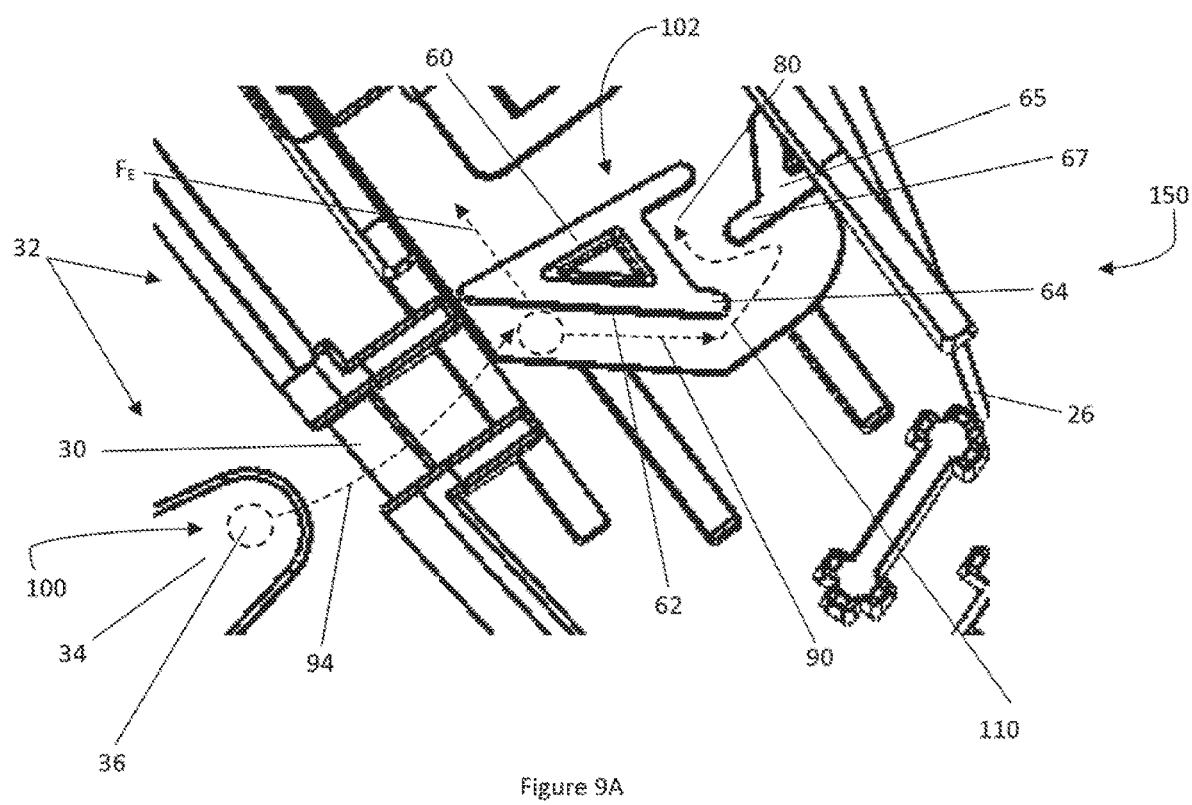
FIG. 9A is a close-up view of a movement path of the bar in the lockable state moving from the home position to the locking position.

FIG. 9A illustrates a close-up view of the closure assembly 32 with the bar arm 34 and bar 36 centered with the latching pathway 30 in the handle 26. The closure assembly 32 includes the bar arm 34, the bar 36, the hook latch 60, and a wall guide unit 65. In the locked state 150, the hook latch 60 starts in a locking position 102. An application of pressure to the trigger (not shown) effectuates an arcuate movement 94 of the bar arm 34 from a home position 100 toward the hook latch 60, through the latching pathway 30. Once the bar 36 passes through the latching pathway 30, the bar 36 begins moving along the pathway and contacts the hook latch 60 where an engaging force $F_E$ is generated on the hook latch 60, causing the hook latch 60 to move in the direction of the engaging force $F_E$. The engaging force $F_E$ is translated into potential energy in the bias member (not shown). As the bar 36 continues to move in the arcuate path 94 the bar 36 slides along an entry portion 62 in the direction 90 and the hook latch 60 continues to move in the direction of the engaging force $F_E$ until the bar 36 passes an entry apex 64. Pressure is then released from the trigger (not shown), which causes the bar 36 to move in the direction of the home position 100. When the bar 36 passes the entry apex 64, the potential energy of the bias member (not shown) is partially released as the hook latch 60 moves in a direction opposite the engaging force $F_E$ until the bar 36 catches on a guide apex 67. When pressure on the trigger (not shown) is released, the bar 36 travels in a locking movement 110 so that the bar 36 passes the guide apex 67 and the potential energy of the bias member (not shown) is released as the hook latch 60 moves in a direction opposite the engaging force $F_E$ until the bar 36 catches in a pocket 80. When in the pocket 80, the bar 36 cannot move until pressure is again applied to the trigger (not shown).

Figure 9B:
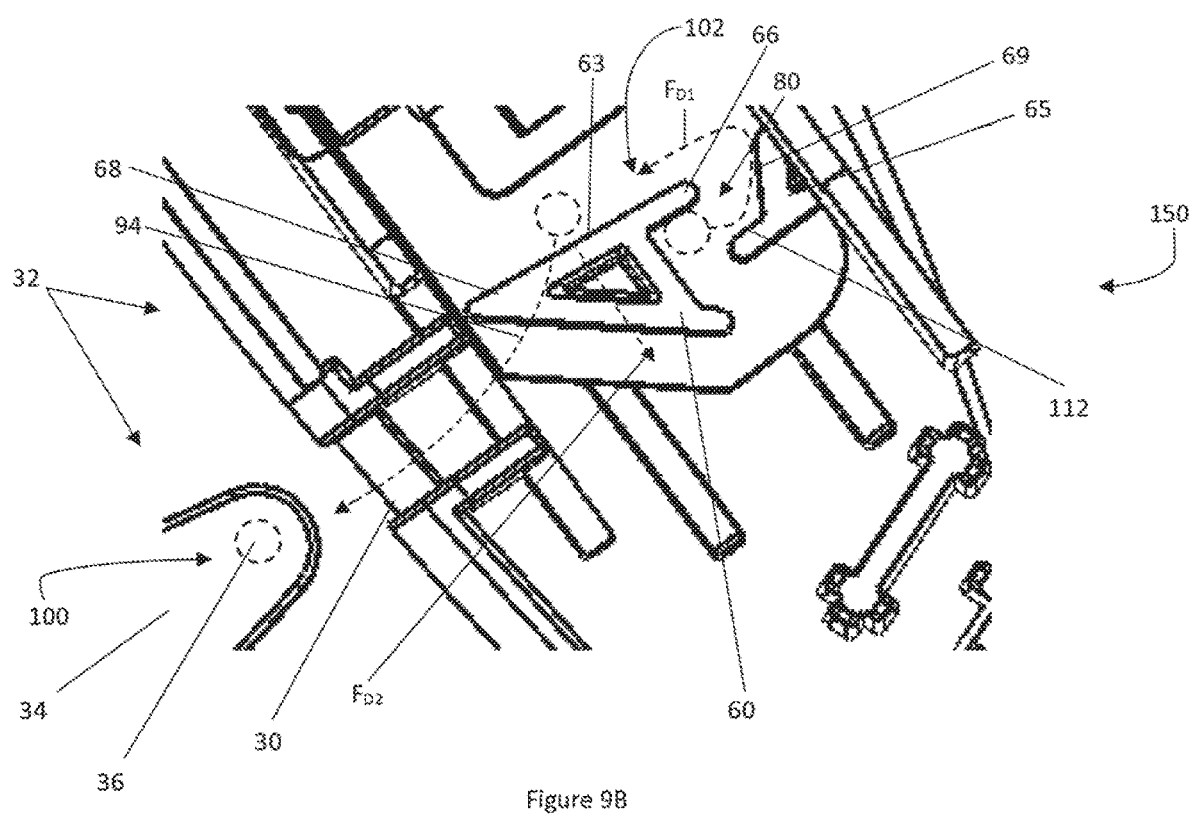
FIG. 9B is a close-up view of a movement path of the bar in the lockable state moving from the locking position to the home position.

FIG. 9B illustrates a close-up view of the closure assembly 32 in the locking state 150 with the bar arm 34 and bar 36 moving along the pathway realign with the latching pathway 30. Once the bar 36 is in the pocket 80, application of pressure on the trigger (not shown) results in the bar 36 traveling in an unlocking movement 112 in a direction away from the home position 100 past an exit apex 66 and against a rear wall 69 of a wall guide 65. The rear wall 69 is configured to contact the bar 36 so that the bar 36 applies a first disengaging force in the direction $F_D$ to the rear wall 69 as the latch plate 52 moves in the direction $F_D$. The movement of the latch plate 52 ensures that the bar 36 will not return to the pocket 80 as the bar 36 moves in the direction of the home position 100 to a location above the return portion 63 of the hook latch 60. When pressure is released on the trigger (not shown), the bar 36 engages in the arcuate movement 94 toward the home position 100. This arcuate movement 94 applies a second disengaging fore in the direction $F_{D2}$ to a return portion 63 of the hook latch 60. The second disengaging force in the direction $F_{D2}$ is translated into potential energy in the bias member (not shown). As the bar 36 continues to move in the arcuate path 94 along the return portion 63, the hook latch 60 continues to move in the direction $F_D$ until the bar 36 passes a release apex 68, at which point the potential energy of the bias member (not shown) is released and the hook latch 60 moves back to the locking position 102.

Figure 9C:
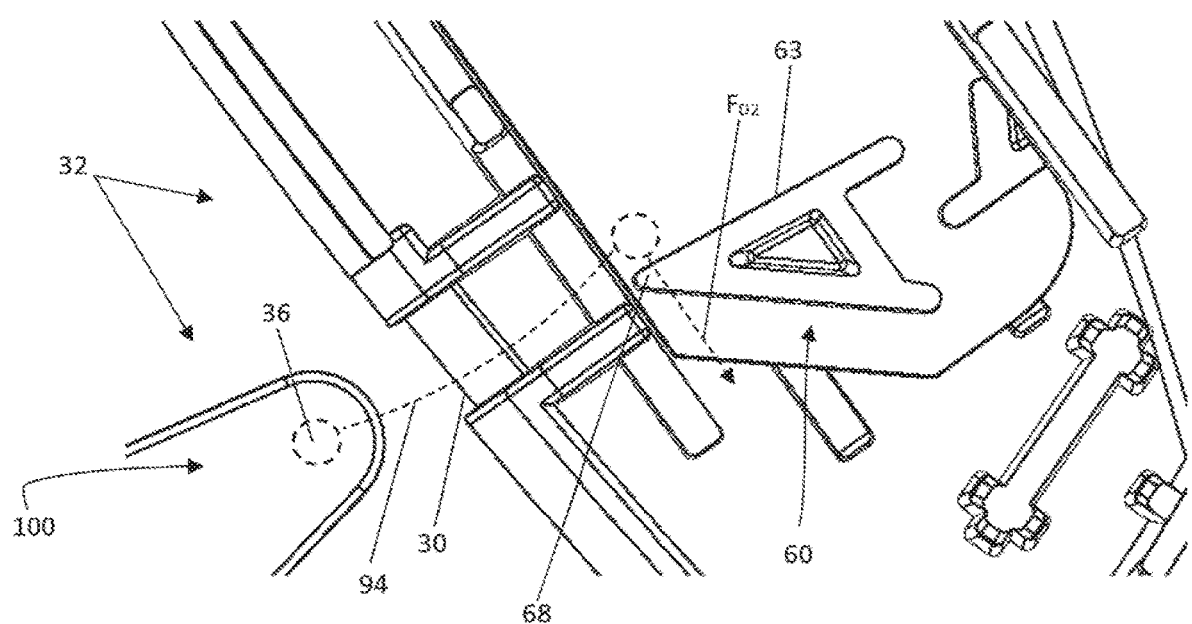
FIG. 9C is a close-up view of a movement path of the bar in a return stroke where the hook latch is moved out of the lathing pathway so that the bar can exit the latch unit.

FIG. 9C shows the closure assembly 32 including the bar 36 moving to the home position 100. The bar 36 in the return stroke moves along an arcuate movement 94 and slides along the return portion 63 toward the release apex 68. As the bar 36 performs the return stroke the bar 36 exerts a force FD2 on the latch unit 60, moving the latch unit 60 in the direction of the force FD2, removing the latch unit 60 from the latching pathway 30. The bar 36 continues to perform the arcuate movement 94, through the latching pathway 30 toward the home position 100.

Figure 9D:
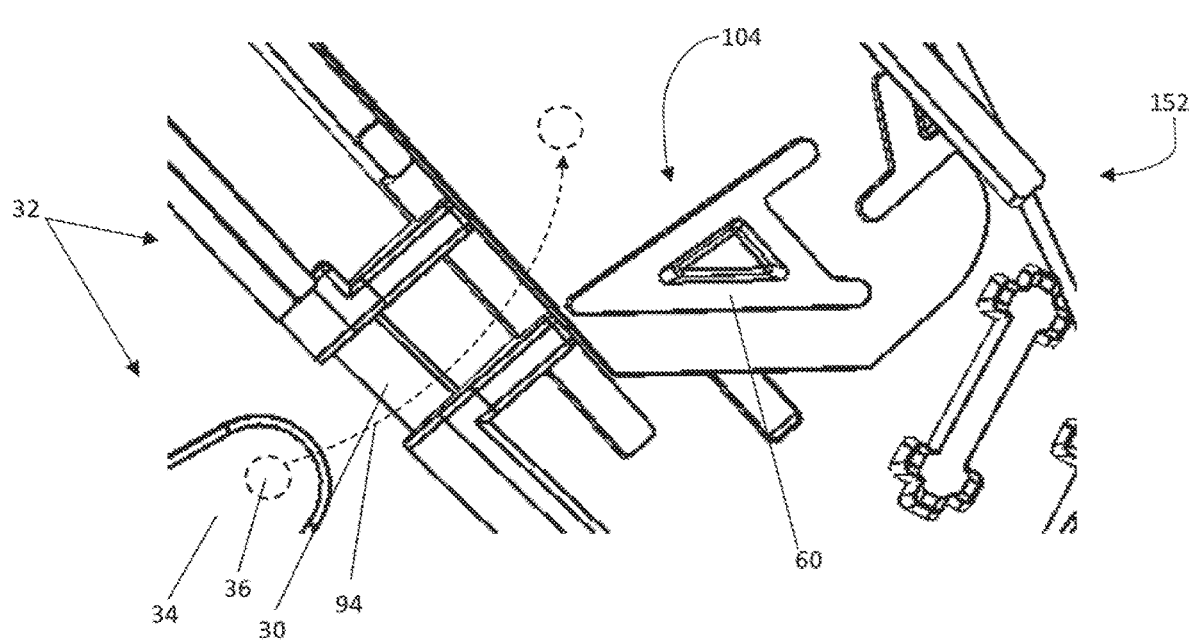
FIG. 9D is a close-up view of the movement path of the bar when the latch unit is in the unlockable state.

FIG. 9D illustrates a close-up view of the closure assembly 32 in the unlocked state 152 where the bar 36 moves in prescribed motion and is mis-aligned with the pathway so that the closure assembly 32 fails to create a locking state. The closure assembly 32 includes the hook latch 60 and the bar arm 34. Affixed to the bar arm 34 is the bar 36. In the unlocked state 152, the hook latch 60 is in an unlocked position 104. Application of pressure to the trigger (not shown) effectuates the arcuate movement 94 of the bar arm 34 and the bar 36 through a latching pathway 30. In the unlocked state 152, the hook latch 60 fails to intersect with the arcuate movement 94 of the bar 36.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

We claim:

1. A closure assembly for a surgical device comprising:
    a latch unit including:
        a hook latch having a home position;
        a forward bias constraint;
        a rearward bias constraint; and
        a bias member extending between and contacting the forward bias constraint and the rearward bias constraint so that the bias member has a pre-load when the hook latch is in the home position; and
    a movement unit including a bar that is movable relative to the latch unit;
    wherein the bar is movable relative to the latch unit in a prescribed motion into contact with the latch unit to create a locked state; and
    wherein the hook latch is movable by the bar in a first direction away from the home position, and wherein the hook latch is movable by the bar in a second direction away from the home position.

2. The closure assembly of claim 1, wherein a loading of the bias member is increased from the pre-load when the hook latch is moved in either the first direction away from the home position or the second direction away from the home position.

3. The closure assembly of claim 2, wherein the bias member contacts a rearward movable bias constraint as a latch plate moves in the first direction so that a load on the bias member is increased relative to the pre-load.

4. The closure assembly of claim 3, wherein the bias member contacts a forward movable bias constraint as the latch plate moves in the second direction so that a load on the bias member is increased relative to the pre-load.

5. The closure assembly of claim 4, wherein the bias member contacts the rearward movable bias constraint when the latch plate moves in the first direction and the bias member contacts the forward movable bias constraint when the latch plate moves in the second direction and the load on the bias member increases relative to the pre-load when the latch plate moves in the first direction and the second direction.

6. The closure assembly of claim 5, wherein the forward movable bias constraint is a forward post or a forward contact surface and the rearward movable bias constraint is a rearward post or a rearward contact surface.

7. The closure assembly of claim 1, wherein the forward bias constraint is a forward post or a forward contact surface and the rearward bias constraint is a rearward post or a rearward contact surface.

8. The closure assembly of claim 1, wherein the bias member is a compression spring that is in contact with both the forward bias constraint and the rearward bias constraint to retain the pre-load on the compression spring.

9. The closure assembly of claim 8, wherein the bias member extends along a longitudinal axis and the forward bias constraint and the rearward bias constraint are connected on a first side, a second side, or both by a side constraint and the side constraint prevents the bias member from extending out of the longitudinal axis.

10. The closure assembly of claim 9, wherein the forward bias constraint includes a forward guide, or the rearward bias constraint includes a rear guide, or both so that a forward movable bias constraint can extend through the forward guide, or a rearward movable bias constraint can extend through the rear guide, or both to increase a load on the bias member above the pre-load.

11. The closure assembly of claim 1, wherein the latch unit includes a selection plate that is movably connected to a latch plate.

12. The closure assembly of claim 11, wherein the selection plate moves the latch unit between a lockable state and an unlockable state.

13. The closure assembly of claim 12, wherein the selection plate includes an unlockable state detent and a lockable state detent that locks the latch unit in the lockable state or the unlockable state.

14. The closure assembly of claim 1, wherein the hook latch is aligned with a latching pathway of the latch unit when the latch unit is in a lockable state so that the bar moves through the latching pathway into contact with the hook latch moving the hook latch in a first direction, and the hook latch is mis-aligned with the latching pathway when the latch unit is in an unlockable state so that as the bar moves through the latching pathway the bar and hook latch are free of contact.

15. A closure assembly for a surgical device comprising:
a latch unit including:
a hook latch having a home position;
a forward bias constraint;
a rearward bias constraint; and
a bias member operably coupled to the forward bias constraint and the rearward bias constraint so that the bias member has a pre-load when the hook latch is in the home position; and a movement unit including a bar that is movable relative to the latch unit so that the bar is movable in a prescribed motion into contact with the latch unit to create a locked state;
wherein the hook latch is movable by the bar in a first direction away from the home position and in a second direction away from the home position.

16. The closure assembly of claim 15, wherein the bias member comprises a compression spring.

17. The closure assembly of claim 15, wherein a loading of the bias member is increased from the pre-load when the hook latch is moved in either the first direction away from the home position or the second direction away from the home position.

18. A closure assembly for a surgical device comprising:
a latch unit including:
a hook latch having a home position;
a forward bias constraint;
a rearward bias constraint; and
a bias member contacting the forward bias constraint and the rearward bias constraint and having a pre-load when the hook latch is in the home position; and
a bar that is movable relative to the latch unit in a prescribed motion, wherein contact between the bar and the latch unit creates a locked state, and wherein the hook latch is movable by the bar in a first direction away from the home position and in a second direction away from the home position.

* * * * *